United States Patent
Gao et al.

(10) Patent No.: US 12,144,248 B2
(45) Date of Patent: Nov. 12, 2024

(54) COMPOUND, DISPLAY PANEL AND DISPLAY APPARATUS

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Wei Gao, Shanghai (CN); Lei Zhang, Shanghai (CN); Wenpeng Dai, Shanghai (CN); Yang Li, Shanghai (CN); Jinghua Niu, Shanghai (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 1018 days.

(21) Appl. No.: 16/732,110

(22) Filed: Dec. 31, 2019

(65) Prior Publication Data

US 2020/0381631 A1 Dec. 3, 2020

(30) Foreign Application Priority Data

May 27, 2019 (CN) .......................... 201910444535.0

(51) Int. Cl.
| | | |
|---|---|---|
| H10K 85/60 | (2023.01) |
| C07D 401/14 | (2006.01) |
| C07D 409/14 | (2006.01) |
| C07F 5/02 | (2006.01) |
| C09K 11/06 | (2006.01) |
| H10K 50/11 | (2023.01) |
| H10K 71/00 | (2023.01) |

(Continued)

(52) U.S. Cl.
CPC ......... *H10K 85/654* (2023.02); *C07D 401/14* (2013.01); *C07D 409/14* (2013.01); *C07F 5/027* (2013.01); *C09K 11/06* (2013.01); *H10K 85/6572* (2023.02); *H10K 85/6576* (2023.02); *C09K 2211/1007* (2013.01); *C09K 2211/1018* (2013.01); *H10K 50/11* (2023.02); *H10K 71/00* (2023.02); *H10K 71/164* (2023.02); *H10K 2101/10* (2023.02); *H10K 2101/30* (2023.02); *H10K 2101/40* (2023.02); *H10K 2102/351* (2023.02)

(58) Field of Classification Search
CPC ............ H10K 85/654; H10K 85/6572; H10K 85/6576; H10K 50/11; H10K 2101/10; C07D 401/14; C07D 409/14; C07F 5/027; C09K 11/06; C09K 2211/1007; C09K 2211/1018
See application file for complete search history.

(56) References Cited

U.S. PATENT DOCUMENTS

2019/0296246 A1* 9/2019 Hayano ................ H10K 85/636

FOREIGN PATENT DOCUMENTS

| CN | 103665014 A | 3/2014 |
| CN | 106916170 A | 7/2017 |

(Continued)

OTHER PUBLICATIONS

CN103665014, machine translation downloaded from Google Patents on Aug. 27, 2022.*
First Office Action mailed Jun. 1, 2021, in corresponding Chinese Patent Application No. 201910444535.0, with English translation, 48 pages.
Gan, L. et al., "Achieving Efficient Triplet Exciton Utilization with Large ΔEST and Nonobvious Delayed Fluorescence by Adjusting Excited State Energy Levels," J. Phys. Chem. Lett., 9(16):4725-4731, Aug. 1, 2018.
Vigante, B. et al., "Synthesis of Linear and V-Shaped Carbazolyl-Substituted Pyridine-3,5-dicarbonitriles Exhibiting Efficient Bipolar Charge Transport and E-Type Fluorescence," Chemistry: A European Journal, 25(13):3325-3336, Feb. 4, 2019.

(Continued)

*Primary Examiner* — Matthew P Coughlin
*Assistant Examiner* — Meghan C Heasley
(74) *Attorney, Agent, or Firm* — CHRISTENSEN O'CONNOR JOHNSON KINDNESS PLLC

(57) ABSTRACT

The present disclosure relates to the technical field of OLED, and provides a compound having TADF property. In an embodiment the compound has a structure according to Formula (1), in which $X_1$-$X_5$ are each independently selected from a carbon atom and a nitrogen atom, and at least one of $X_1$-$X_5$ is a nitrogen atom; $R_{11}$-$R_{20}$ are each selected from the group consisting of a hydrogen atom, a fluorine atom, alkyl, alkoxy, cyano, trifluoromethyl, an electron-accepting group, and an electron-donating group; at least one of $R_{11}$-$R_{15}$ is an electron-donating group or an electron-accepting group, and at least one of $R_{16}$-$R_{20}$ is an electron-donating group or an electron-accepting group; when each of $R_{11}$-$R_{15}$ is an electron-accepting group, at least one of $R_{16}$-$R_{20}$ is an electron-donating group, and each of $R_{11}$-$R_{15}$ is an electron-donating group, at least one of $R_{16}$-$R_{20}$ is an electron-accepting group.

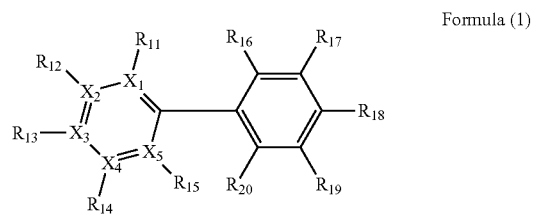

Formula (1)

4 Claims, 3 Drawing Sheets

(51) Int. Cl.
*H10K 71/16* (2023.01)
*H10K 101/10* (2023.01)
*H10K 101/30* (2023.01)
*H10K 101/40* (2023.01)
*H10K 102/00* (2023.01)

(56) References Cited

FOREIGN PATENT DOCUMENTS

| | | | |
|---|---|---|---|
| CN | 107531628 A | 1/2018 | |
| CN | 107667102 A | 2/2018 | |
| CN | 108997322 A | 12/2018 | |
| DE | 102016115853 A1 | 3/2018 | |
| IN | 108864054 A | 11/2018 | |
| WO | WO2015175678 | * 5/2015 | ............. C09K 11/06 |
| WO | 2016/208240 A1 | 12/2016 | |

OTHER PUBLICATIONS

Sun, Y. and Wang, S., "Extending π-Conjugation of Triarylborons with a 2,2-Bpy Core: Impact of Donor-Acceptor Geometry on Luminescence, Anion Sensing, and Metal Ion Binding," Inorg. Chem., 49(10):4394-4404, Apr. 23, 2010.

* cited by examiner

COMPOUND, DISPLAY PANEL AND DISPLAY APPARATUS

CROSS-REFERENCE TO RELATED APPLICATIONS

The present disclosure claims priority to Chinese Patent Application No. 201910444535.0, filed on May 27, 2019, the content of which is incorporated herein by reference in its entirety.

FIELD

The present disclosure relates to the technical field of organic electroluminescent materials, and in particular, to a material having thermally activated delayed fluorescence (TADF) property, as well as a display panel and a display apparatus including the compound.

BACKGROUND

With the development of electronic display technology, Organic Light-Emitting Diodes (OLEDs) are widely used in various display apparatuses, and research on the light-emitting materials of OLEDs are also more extensive.

Based on the light-emitting mechanism, materials for a light-emitting layer of an OLED can be generally divided into four types:

(1) fluorescent materials; (2) phosphorescent materials; (3) triplet-triplet annihilation (TTA) materials; (4) thermally activated delayed fluorescence (TADF) materials.

Regarding the fluorescent materials, according to spin-statistics, a ratio of singlet excitons to triplet excitons is 1:3, and thus the maximum internal quantum yield of fluorescent materials does not exceed 25%. According to the Lambertian luminescence mode, the light extraction efficiency is about 20%, and thus an external quantum efficiency (EQE) of the OLED device based on the fluorescent material does not exceed 5%.

With respect to the phosphorescent materials, an intersystem crossing of molecules can be enhanced due to a heavy atom effect of the phosphorescent materials, and 75% of triplet excitons can be directly utilized to complete emission involving both S1 and T1 at room temperature, where a theoretical maximum internal quantum yield can reach 100%. According to the Lambertian luminescence mode, a light extraction efficiency is about 20%, and thus the EQE of the OLED device based on the phosphorescent materials can reach 20%. However, the phosphorescent materials are conventionally complexes of heavy metals, such as Ir, Pt, Os, Re, Ru, etc., and are unsuitable for a large-scale production due to the attendant high production costs. Under a high electric current density, a substantial efficiency fall can be observed in the phosphorescent materials, which lead to a deterioration of the stability of the phosphorescent devices.

Regarding TAA materials, two adjacent triplet excitons are combined to form a singlet excited state molecule with a higher energy level and a ground state molecule. However, since two triplet excitons merely produce one singlet state exciton, the theoretical maximum internal quantum yield can only reach 62.5%. In order to prevent a substantial fall of efficiency, a concentration of triplet excitons should be regulated during this process.

For the TADF materials, when an energy level difference between the singlet excited state and the triplet excited state is relatively small, a reverse intersystem crossing (RISC) may occur among the molecules, and the excitons are converted from T1 state to S1 state by absorbing the ambient heat, so that 75% of triplet excitons and 25% of singlet excitons can be utilized at the same time. In this way, the theoretical maximum internal quantum yield can reach 100%. The TADF materials are mainly organic compounds without rare metal elements, so that the production cost is relatively low. The TADF materials can be chemically modified by various methods. However, there are few TADF materials that have been discovered so far, and it is urgent to develop new TADF materials applicable in OLED devices.

SUMMARY

In view of the above, the present disclosure provides a compound having TADF property, and the compound has a structure according to Formula (1):

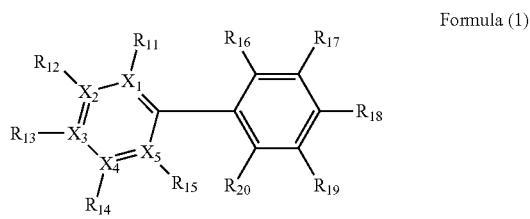

Formula (1)

wherein $X_1$-$X_5$ are each independently selected from a carbon atom and a nitrogen atom, and at least one of $X_1$-$X_5$ is a nitrogen atom;

$R_{11}$-$R_{20}$ are each selected from the group consisting of a hydrogen atom, a fluorine atom, alkyl, alkoxy, cyano, trifluoromethyl, an electron-accepting group, and an electron-donating group;

at least one of $R_{11}$-$R_{15}$ is an electron-donating group or an electron-accepting group, at least one of $R_{16}$-$R_{20}$ is an electron-donating group or an electron-accepting group, and $R_{11}$-$R_{15}$ and $R_{16}$-$R_{20}$ are not all electron-donating groups or electron-accepting groups;

when each of $R_{11}$-$R_{15}$ is an electron-accepting group, at least one of $R_{16}$-$R_{20}$ is an electron-donating group, and when each of $R_{11}$-$R_{15}$ is an electron-donating group, at least one of $R_{16}$-$R_{20}$ is an electron-accepting group;

the electron-donating group is selected from the group consisting of a substituted or unsubstituted C12-C40 carbazolyl and derivatives thereof, a substituted or unsubstituted C12-C40 diphenylamino and derivatives thereof, a substituted or unsubstituted C18-C60 triphenylamino and derivatives thereof, and a substituted or unsubstituted C13-C40 acridinyl and derivatives thereof; and the electron-accepting group is selected from the group consisting of an aryl boron-based group, a nitrogen-containing heterocyclic group, a cyano-containing group, a carbonyl-containing group, a fluorine-containing group, a sulfone-based group, and a phosphoroso-containing group.

The present disclosure also provides a display panel, including an organic light-emitting device, the organic light-emitting device comprising an anode; a cathode; and a light-emitting layer disposed between the anode and the cathode. A light-emitting material of the light-emitting layer includes one or more of the compounds according the present disclosure.

The present disclosure also provides a display apparatus, including the display panel according to the present disclosure.

DESCRIPTION OF EMBODIMENTS

Figure 1:
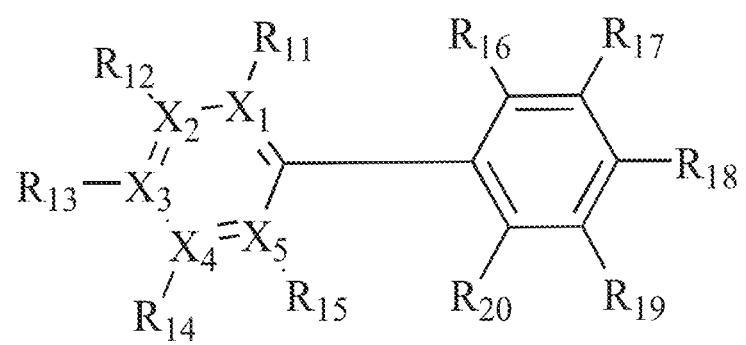
FIG. 1 is a general formula of a compound according to an embodiment of the present disclosure.
Figure 2:
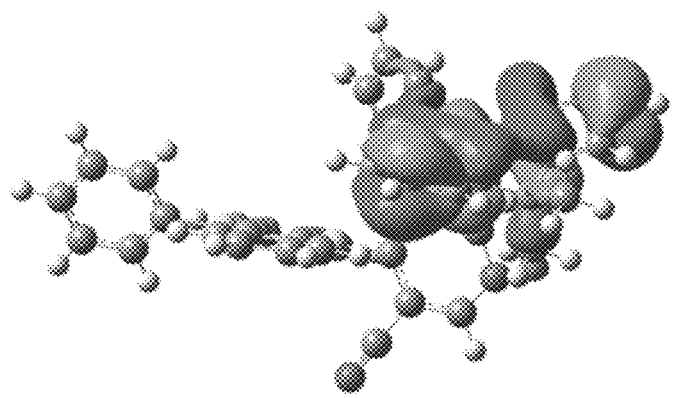
FIG. 2 is an energy level diagram of HOMO of an exemplary Compound P6 according to an embodiment of the present disclosure.
Figure 3:
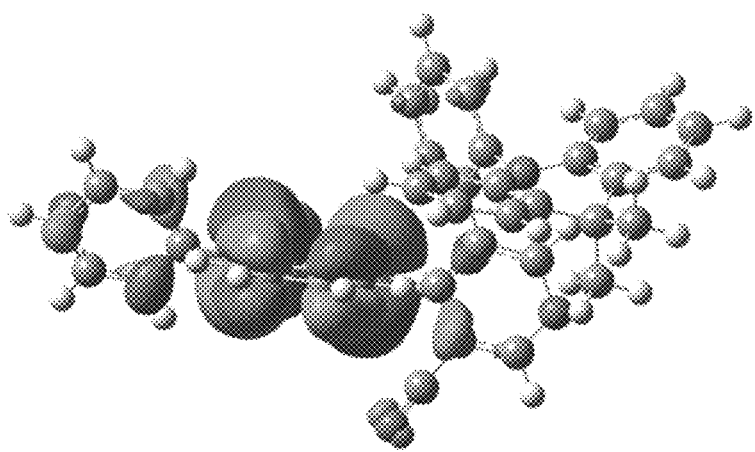
FIG. 3 is an energy level diagram of LUMO of the exemplary Compound P6 according to an embodiment of the present disclosure.

The present disclosure is further explained with Examples and Comparative Examples, which are merely intended to describe the present disclosure, and the present disclosure is not limited thereto.

In an aspect, the present disclosure provides a compound having a structure according to Formula (1):

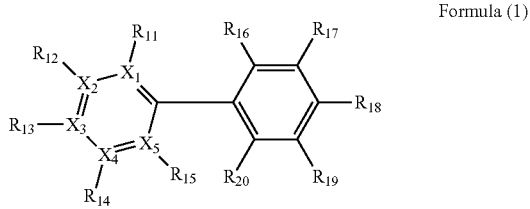

Formula (1)

wherein $X_1$-$X_5$ are each independently selected from a carbon atom and a nitrogen atom, and at least one of $X_1$-$X_5$ is a nitrogen atom;

$R_{11}$-$R_{20}$ are each selected from the group consisting of a hydrogen atom, a fluorine atom, alkyl, alkoxy, cyano, trifluoromethyl, an electron-accepting group, and an electron-donating group;

at least one of $R_{11}$-$R_{15}$ is an electron-donating group or an electron-accepting group, at least one of $R_{16}$-$R_{20}$ is an electron-donating group or an electron-accepting group, and $R_{11}$-$R_{15}$ and $R_{16}$-$R_{20}$ are not all electron-donating groups or electron-accepting groups;

when each of $R_{11}$-$R_{15}$ is an electron-accepting group, at least one of $R_{16}$-$R_{20}$ is an electron-donating group, and when each of $R_{11}$-$R_{15}$ is an electron-donating group, at least one of $R_{16}$-$R_{20}$ is an electron-accepting group;

the electron-donating group is selected from the group consisting of a substituted or unsubstituted C12-C40 carbazolyl and derivatives thereof, a substituted or unsubstituted C12-C40 diphenylamino and derivatives thereof, a substituted or unsubstituted C18-C60 triphenylamino and derivatives thereof, and a substituted or unsubstituted C13-C40 acridinyl and derivatives thereof; and the electron-accepting group is selected from the group consisting of an aryl boron-based group, a nitrogen-containing heterocyclic group, a cyano-containing group, a carbonyl-containing group, a fluorine-containing group, a sulfone-based group, and a phosphoroso-containing group.

According to an embodiment of the compound of the present disclosure, at least one of $R_{11}$-$R_{15}$ is an electron-donating group or an electron-accepting group, and at least one of $R_{16}$-$R_{20}$ is an electron-donating group or an electron-accepting group. In the present embodiment, two D-A structures are included in the same molecule, such that the molecule has a dual emission characteristic, thereby achieving a higher photoluminescence quantum yield (PLQY). Compared with a single-emitting core, a compound molecule containing two emitting units has higher vibrator strength, stronger absorption and emission, and thus improves a light-emitting efficiency of the device.

According to an embodiment of the compound of the present disclosure, at least two of $R_{11}$-$R_{15}$ are different electron-accepting groups, and at least one of $R_{16}$-$R_{20}$ is an electron-donating group. In the compound according to Formula (1), the at least two electron-accepting groups are bonded via a nitrogenous heterocycle, and the at least one electron-donating group is bonded to a benzene ring. In this way, the HOMO of the molecule is configured to be better dispersed, and an overlapping degree of HOMO and LUMO tracks of the compound molecule is increased, thereby increasing the vibrator strength, enhancing the PLQY, and improving the light-emitting efficiency.

According to an embodiment of the compound of the present disclosure, at least one of $R_{11}$-$R_{15}$ is an electron-accepting group, and at least two of $R_{16}$-$R_{20}$ is electron-donating groups. Similarly, in the compound represented by formula (1), the at least one electron-accepting group is bonded to a nitrogenous heterocycle, and the at least two electron-donating groups are bonded via a benzene ring. In this way, a better separation of HOMO and LUMO can be achieved, the overlapping degree of HOMO and LUMO tracks of the compound molecule is increased, thereby increasing the vibrator strength, enhancing the PLQY, and improving the light-emitting efficiency.

According to an embodiment of the compound of the present disclosure, at least one of $R_{11}$ and $R_{15}$ is the electron-donating group or the electron-accepting group, and at least one of $R_{16}$ and $R_{20}$ is the electron-donating group or the electron-accepting group. In the present embodiment, $R_{11}$, $R_{15}$, $R_{16}$ and $R_{20}$ are located at positions adjacent to the connection, which has the following advantages: (1) the compound having such an arrangement of electron-donating groups and electron-accepting groups has the D-A type molecular structure, which is conducive to an effective separation of HOMO and LUMO; (2) the dihedral angle between D unit and A unit is increased by the adjacent connection of D unit and A unit, so that there is a large steric hindrance between D unit and A unit, thereby obtaining a smaller $\Delta E_{st}$; (3) the spatial constraint effect in the molecule is increased, which can reduce the positive solvation discoloration effect of the molecule, while improving the molecular luminescence color purity and achieving a smaller peak width at half height.

According to an embodiment of the compound of the present disclosure, the aryl boron-based electron-accepting group is any one of the following groups:

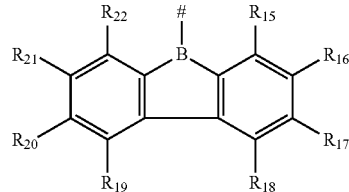

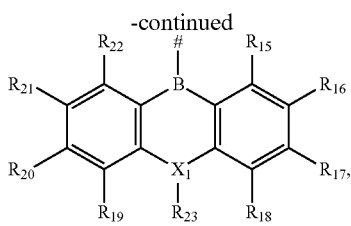

in which $R_{15}$-$R_{23}$ are each independently selected from the group consisting of alkyl, alkoxy, aryl, and heteroaryl;

$X_1$ is selected from the group consisting of a boron atom, an oxygen atom, a sulfur atom, and a nitrogen atom, and when $X_1$ is an oxygen atom or a sulfur atom, $R_{23}$ is absent; and # indicates a bonding position.

In this embodiment, the boron-containing unit has excellent photophysical and electrochemical properties, the boron atom can form a p-π conjugated structure, such that the compound molecule has a lower LUMO track; and in the meantime, the boron-containing cyclic structure is a rigid structure, and has a smaller peak width at half height in the emission spectrum. In particular, in the aryl boron-based electron-accepting group of the present embodiment, when $R_{15}$ and $R_{22}$ are alkyl and/or alkoxy, the boron atom can be protected from being attacked by water and oxygen.

According to an embodiment of the compound of the present disclosure, the aryl boron-based electron-accepting group is any one of the following groups:

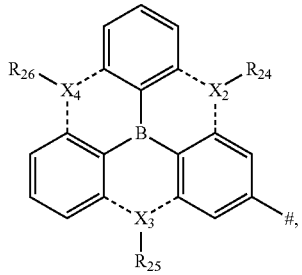

$R_{24}$-$R_{26}$ are each independently selected from the group consisting of alkyl, alkoxy, aryl, and heteroaryl;

$X_2$-$X_4$ has at least one bonded to an adjacent benzene ring and are each independently selected from the group consisting of a boron atom, an oxygen atom, a sulfur atom, and a nitrogen atom, and when $X_2$-$X_4$ are each an oxygen atom or a sulfur atom, $R_{24}$-$R_{26}$ are absent; and # indicates a bonding position.

According to an embodiment of the compound of the present disclosure, the aryl boron-based electron-accepting group is any one of the following groups:

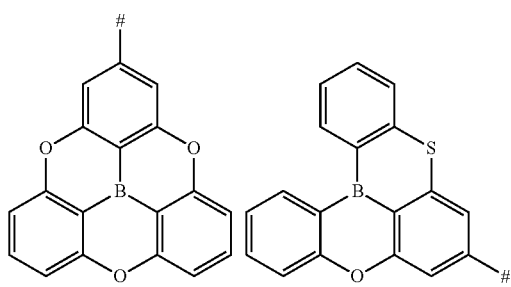

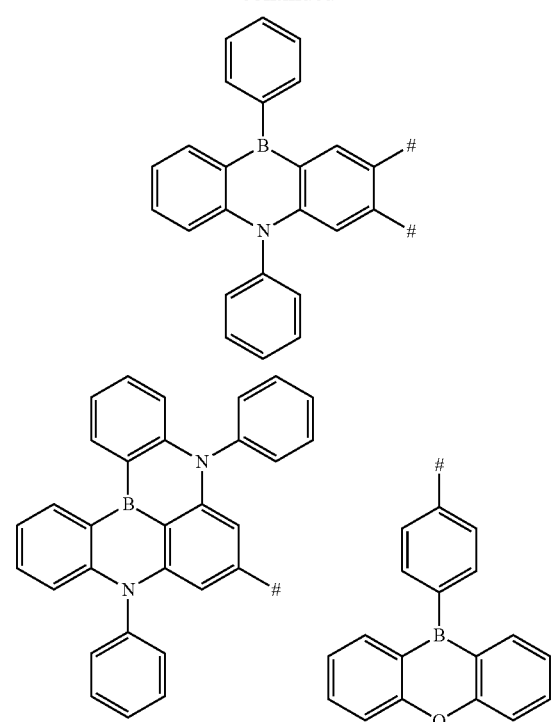

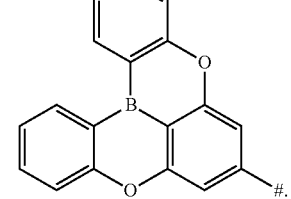

In the boron heterocyclic compound of the present embodiment, the compound molecule can form a resonance structure, and has a greater rigidity, which reduces the peak width at half height of an emission wavelength, thereby improving the color purity and saturation of the organic light-emitting device.

According to an embodiment of the compound of the present disclosure, the nitrogen-containing heterocyclic group is according to any one of the following formulas:

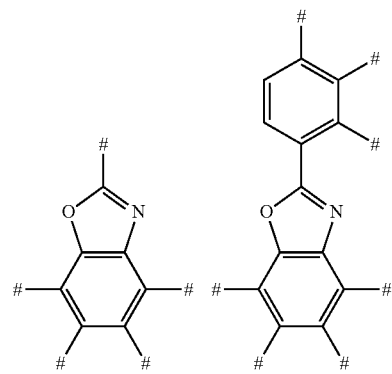

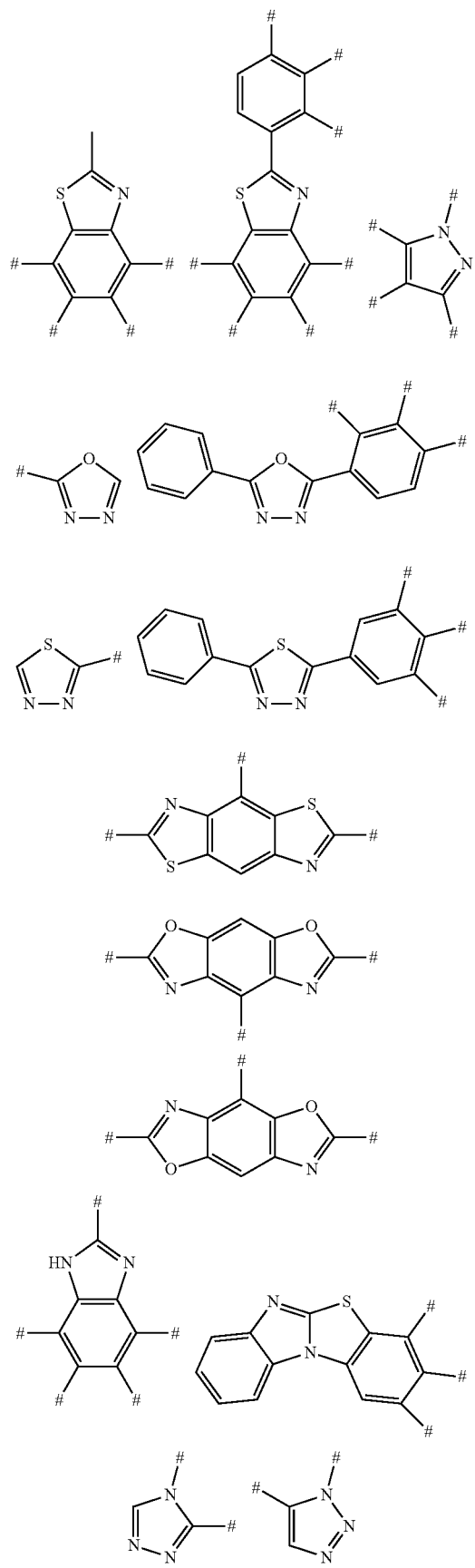
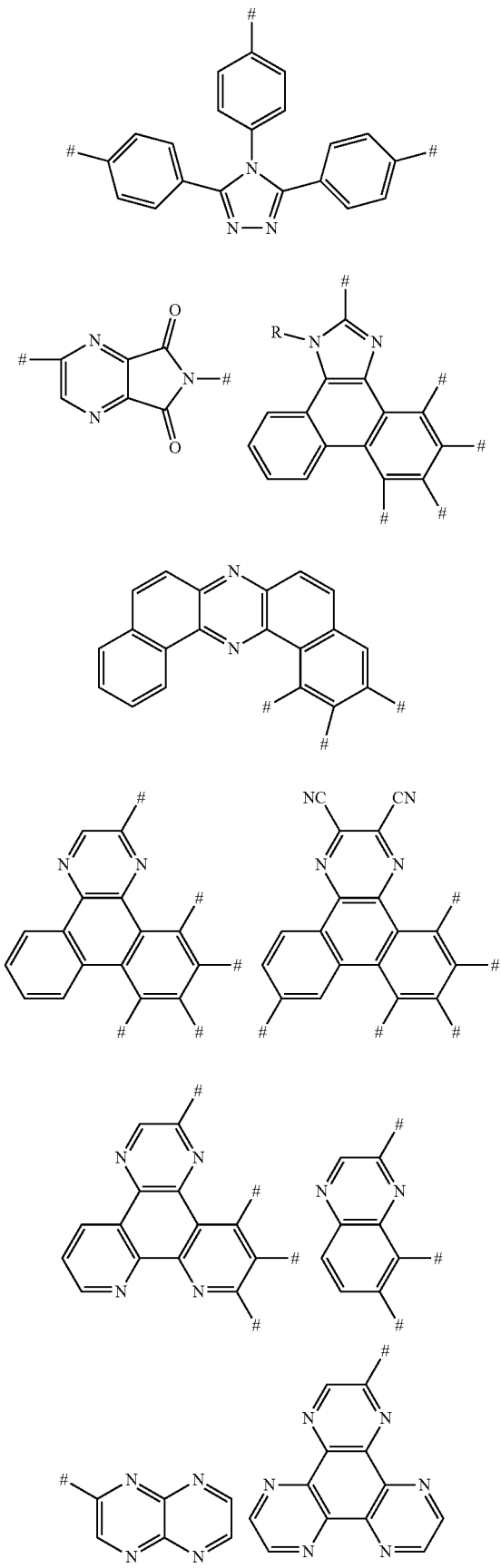

-continued
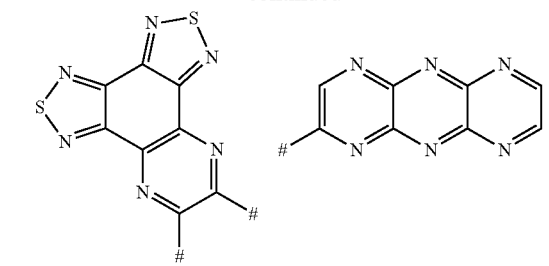
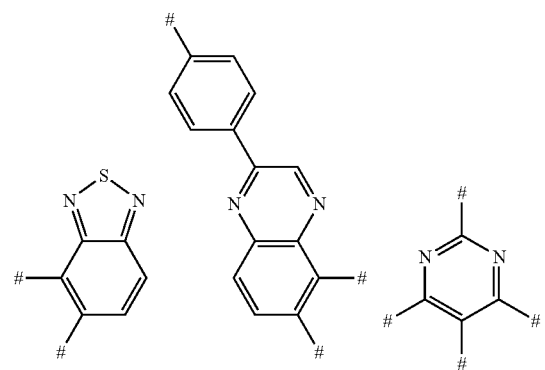
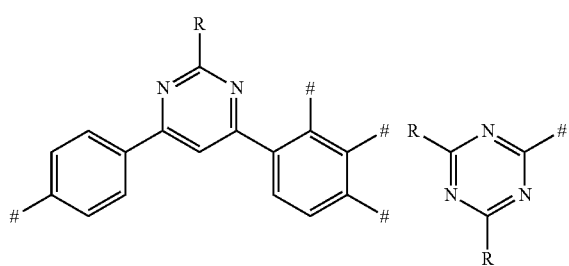
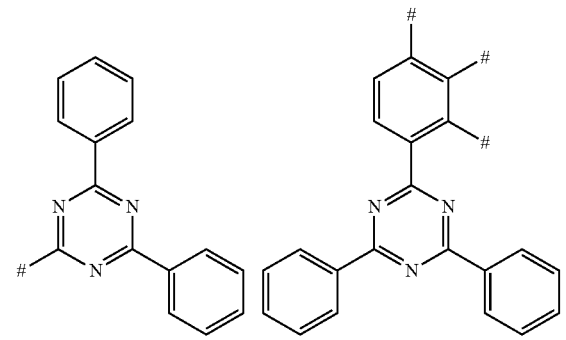
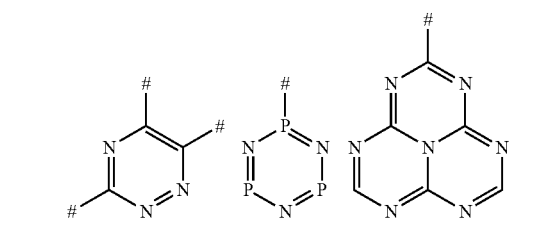
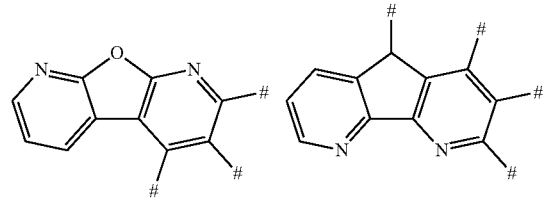
-continued
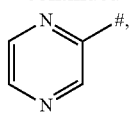
wherein # indicates a bonding position; and
R is selected from the group consisting of a hydrogen atom, C1-C20 alkyl, C1-C20 alkoxy, C4-C8 cycloalkyl, C6-C40 aryl, and C4-C40 heteroaryl.
According to an embodiment of the compound of the present disclosure, the cyano-containing group is any one of the following groups:
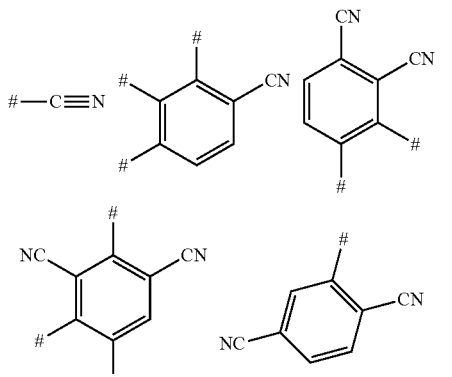
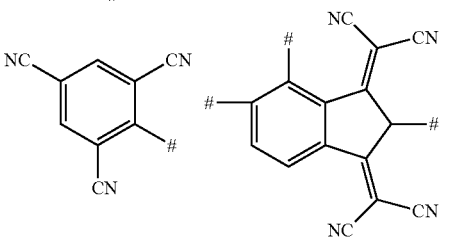
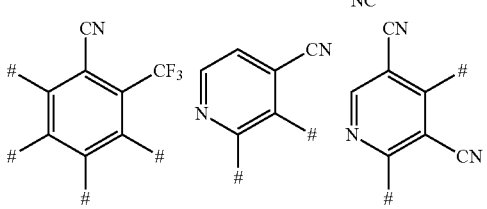
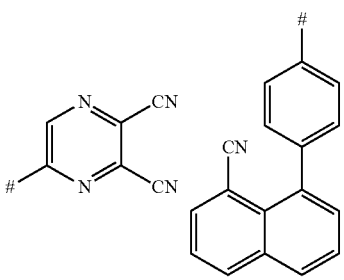
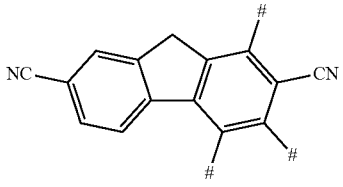

-continued

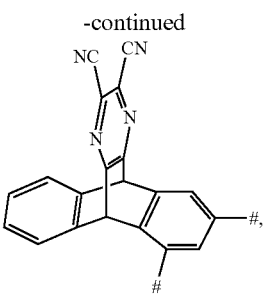

wherein # indicates a bonding position.

According to an embodiment of the compound of the present disclosure, the sulfone-based group is any one of the following groups:

According to an embodiment of the compound of the present disclosure, the phosphoroso-containing group is according to any one of the following formulas:

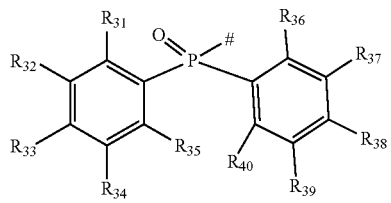

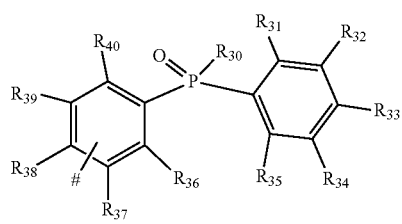

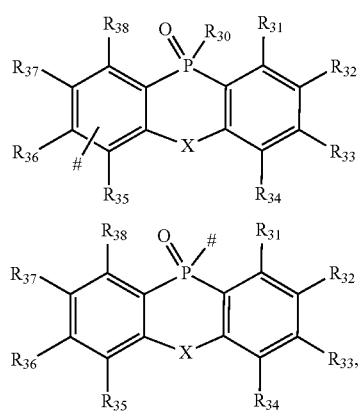

wherein

X is any one of O, S, —$BR_{41}$—, —$C(R_{41})_2$—, —$Si(R_{41})_2$—, or —$NR_{41}$—;

$R_{30}$, $R_{31}$, $R_{32}$, $R_{33}$, $R_{34}$, $R_{35}$, $R_{36}$, $R_{37}$, $R_{38}$, $R_{39}$, $R_{40}$ and $R_{41}$ are each independently selected from the group consisting of a hydrogen atom, a substituted or unsubstituted C1-C20 alkyl, a substituted or unsubstituted C3-C20 cycloalkyl, a substituted or unsubstituted C1-C20 alkoxy, a substituted or unsubstituted C3-C20 heterocyclic group, a substituted or unsubstituted C6-C40 aryl, and a substituted or unsubstituted C2-C40 heteroaryl; and # indicates a bonding position.

According to an embodiment of the compound of the present disclosure, the carbonyl-containing group is according to any one of the following formulas:

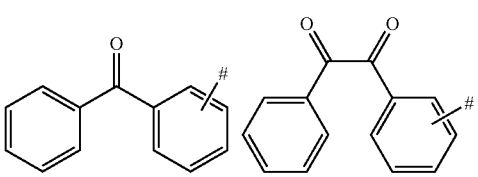

-continued
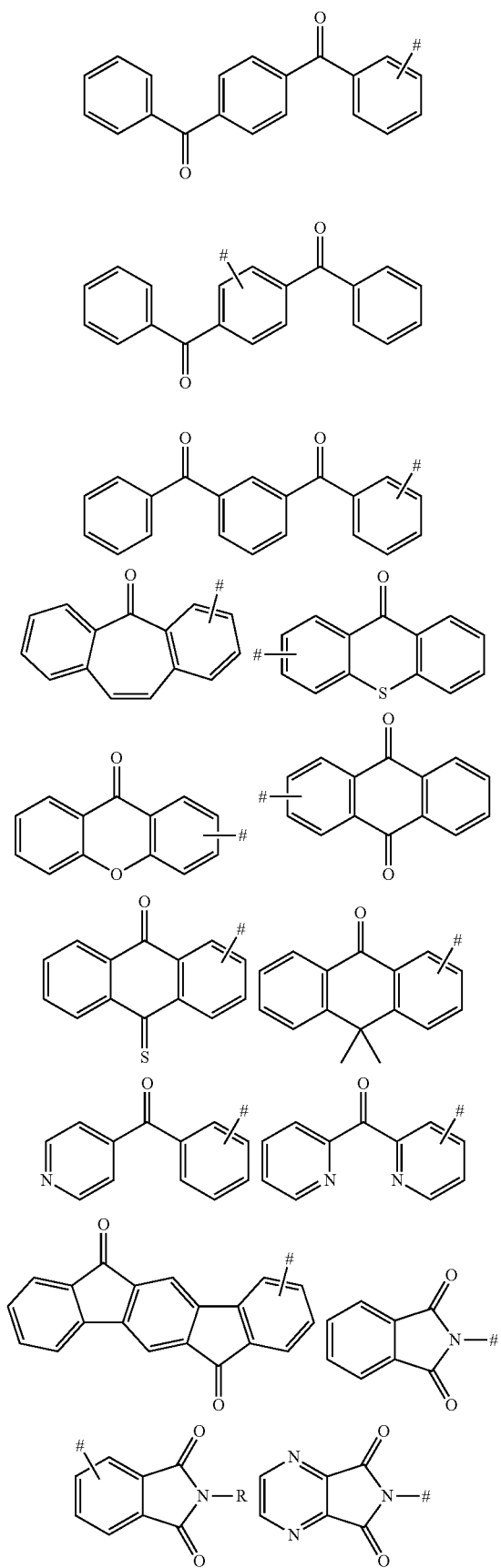
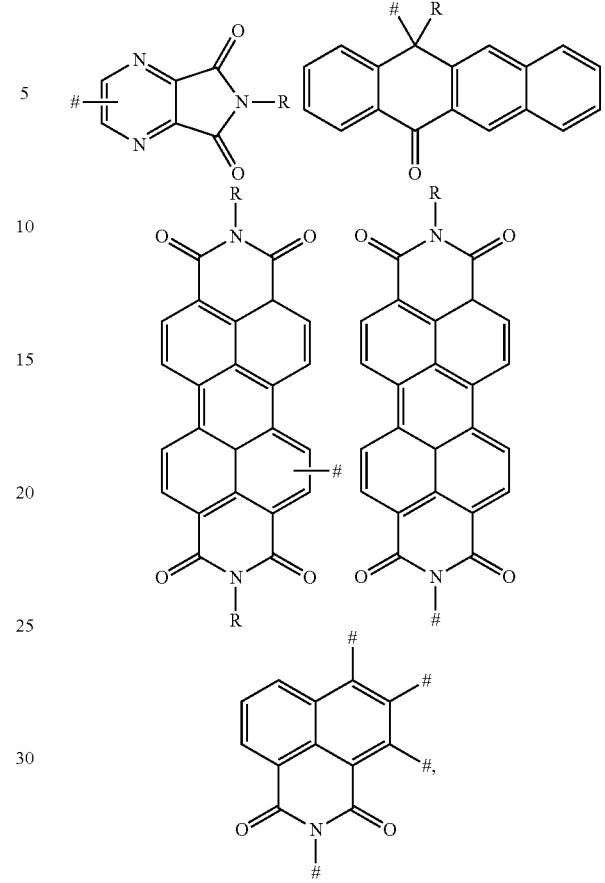
wherein R represents C1-C20 alkyl, C1-C20 alkoxy, C2-C20 alkenyl, C2-C20 alkynyl, C4-C8 cycloalkyl, C6-C40 aryl, or C4-C40 heteroaryl; and
# indicates a bonding position to the Formula (1).
According to an embodiment of the compound of the present disclosure, the electron-donating group is any one or more of the following groups:
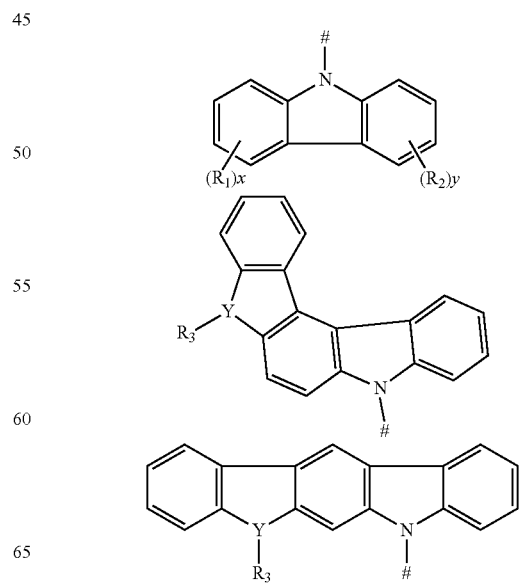

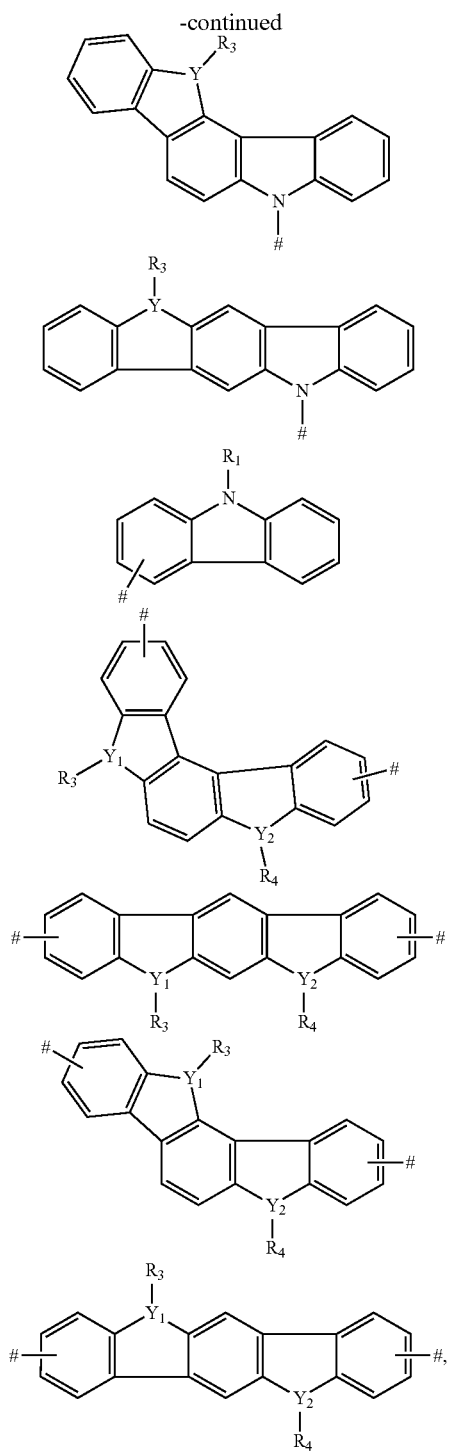

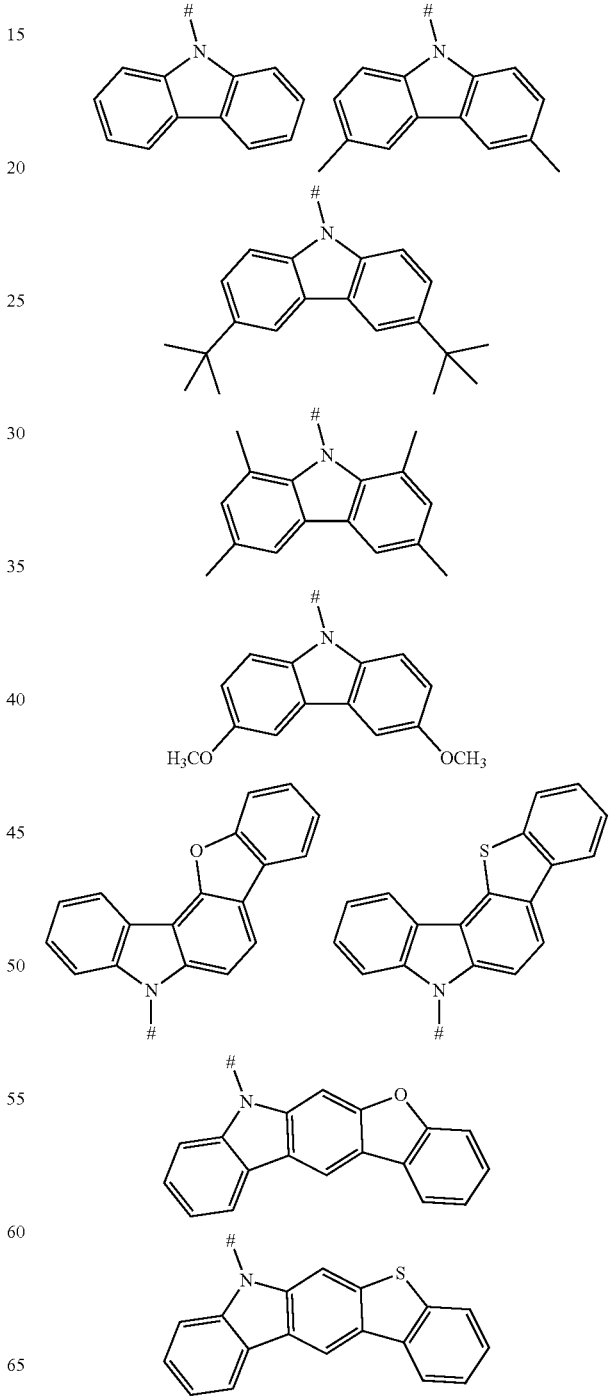

thereof, a substituted or unsubstituted C12-C40 diphenylamino and derivatives thereof, and a substituted or unsubstituted C3-C40 azinyl and derivatives thereof; and when Y is an oxygen atom or a sulfur atom, $R_3$ is absent; when $Y_1$ is an oxygen atom or a sulfur atom, $R_3$ is absent; and when $Y_2$ is an oxygen atom or a sulfur atom, $R_4$ is absent.

According to an embodiment of the compound of the present disclosure, the electron-donating group is according to any one or more of the following formulas:

wherein Y, $Y_1$ and $Y_2$ are each independently selected from the group consisting of a carbon atom, a nitrogen atom, an oxygen atom, a sulfur atom and a silicon atom;

x and y are each an integer independently selected from 0, 1, 2 or 3;

# indicates a bonding position to the Formula (1);

$R_1$, $R_2$, $R_3$ and $R_4$ are each independently selected from the group consisting of a hydrogen atom, C1-C20 alkyl, C1-C20 alkoxy, a substituted or unsubstituted C6-C40 aryl, a substituted or unsubstituted C4-C40 heteroaryl, a substituted or unsubstituted C12-C40 carbazolyl and derivatives

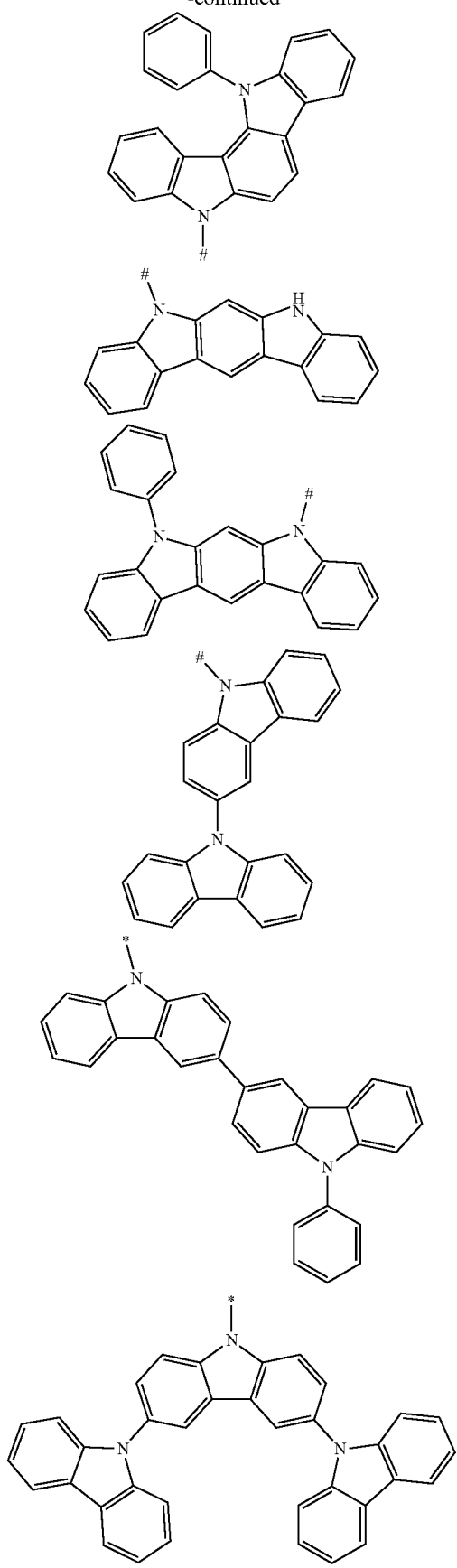
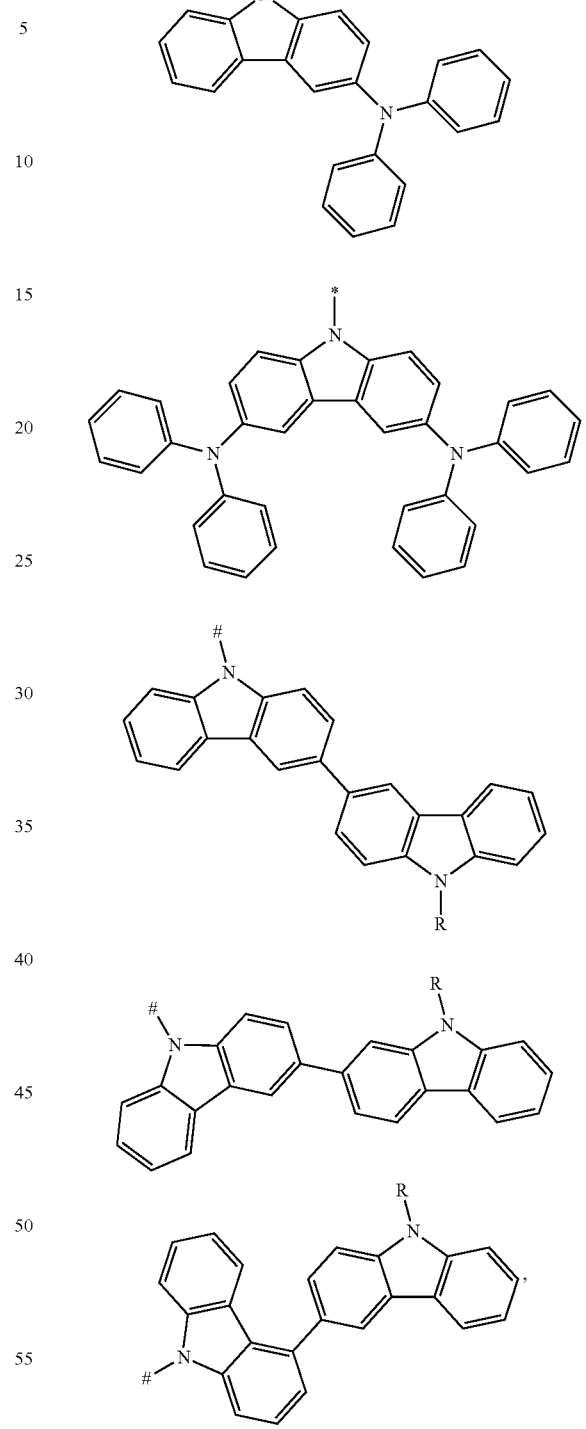
wherein R represents C1-C20 alkyl, C1-C20 alkoxy, C2-C20 alkenyl, C2-C20 alkynyl, C6-C40 aryl, or C4-C40 heteroaryl; and
\# indicates a bonding position to the Formula (1).
According to an embodiment of the compound of the present disclosure, the electron-donating group is any one or more of the following formulas:

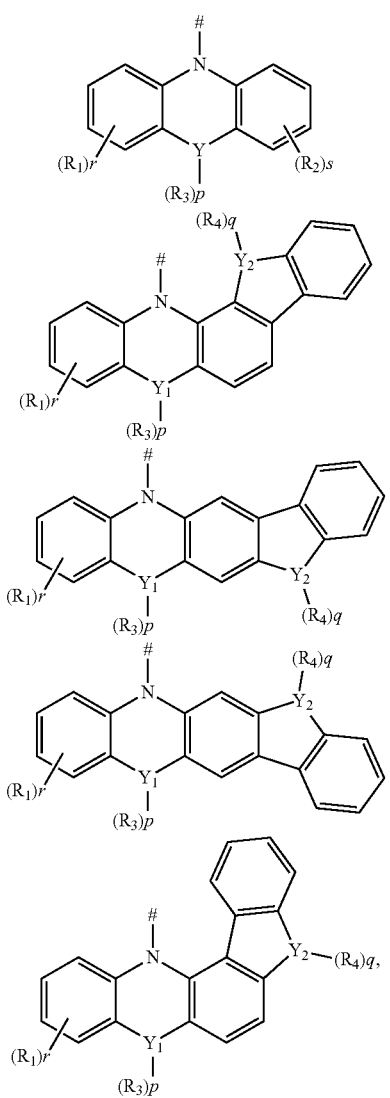

in which Y, $Y_1$ and $Y_2$ are each independently selected from the group consisting of a carbon atom, a nitrogen atom, an oxygen atom, a sulfur atom and a silicon atom;

\# indicates a bonding position to the Formula (1);

r and s are each an integer independently selected from 0, 1, 2 or 3;

p and q are each an integer independently selected from 0, 1, or 2;

$R_1$, $R_2$, $R_3$ and $R_4$ are each independently selected from the group consisting of a hydrogen atom, C1-C20 alkyl, C1-C20 alkoxy, a substituted or unsubstituted C6-C40 aryl, a substituted or unsubstituted C4-C40 heteroaryl, a substituted or unsubstituted C12-C40 carbazolyl and derivatives thereof, a substituted or unsubstituted C12-C40 diphenylamino and derivatives thereof, a substituted or unsubstituted C13-C40 acridinyl and derivatives thereof, and a substituted or unsubstituted C3-C40 azinyl and derivatives thereof; and when Y, $Y_1$ or $Y_2$ is an oxygen atom or a sulfur atom, p is 0 or q is 0; when Y, $Y_1$ or $Y_2$ is a nitrogen atom, p and q are each an integer independently selected from 0 or 1; when Y, $Y_1$ or $Y_2$ is a carbon atom or a silicon atom, p and q are each an integer independently selected from 0, 1, or 2.

According to an embodiment of the compound of the present disclosure, the electron-donating group is any one or more of the following groups:

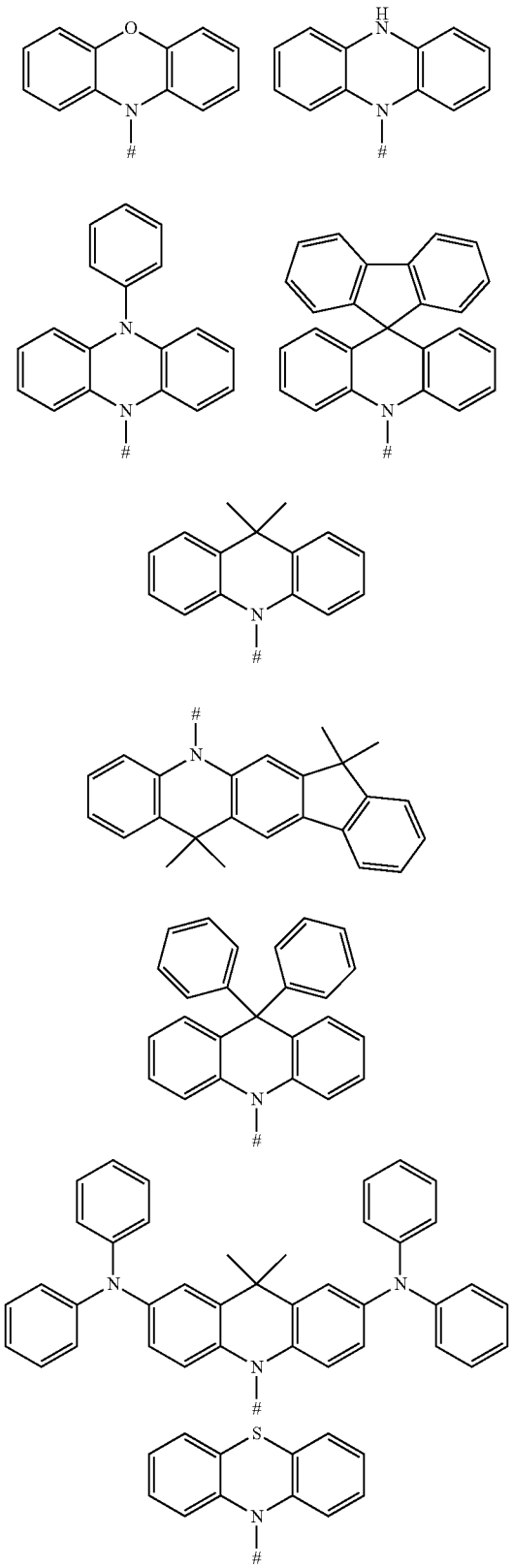

-continued

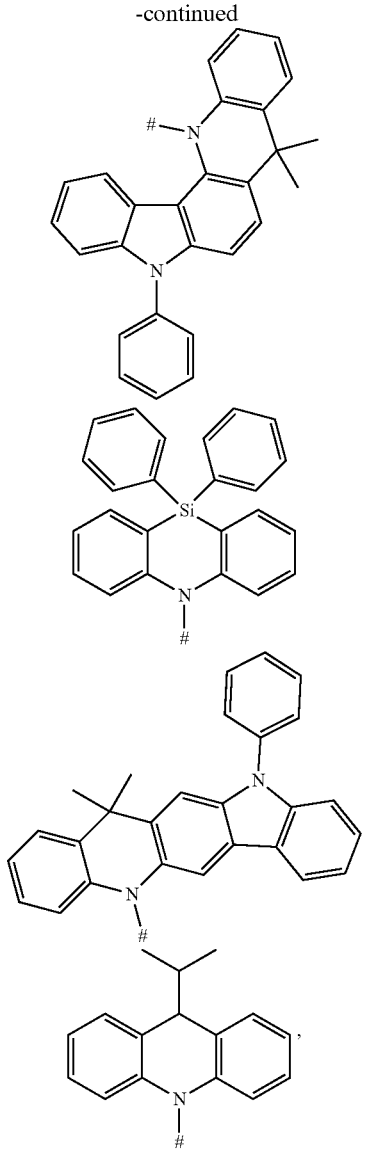

in which # indicates a bonding position to the Formula (1).

According to an embodiment of the compound of the present disclosure, the electron-donating group is any one or more of the following groups:

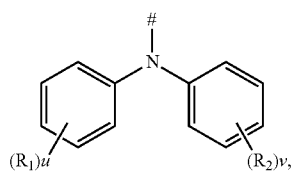

in which # indicates a bonding position to the Formula (1);
u and v are each an integer independently selected from 0, 1, 2 or 3;
R₁ and R₂ are each independently selected from the group consisting of a hydrogen atom, C1-C20 alkyl, C1-C20 alkoxy, a substituted or unsubstituted C6-C40 aryl, a substituted or unsubstituted C4-C40 heteroaryl, a substituted or unsubstituted C12-C40 carbazolyl and derivatives thereof, a substituted or unsubstituted C12-C40 diphenylamino and derivatives thereof, and a substituted or unsubstituted C3-C40 azinyl and derivatives thereof.

According to an embodiment of the compound of the present disclosure, the electron-donating group is any one or more of the following groups:

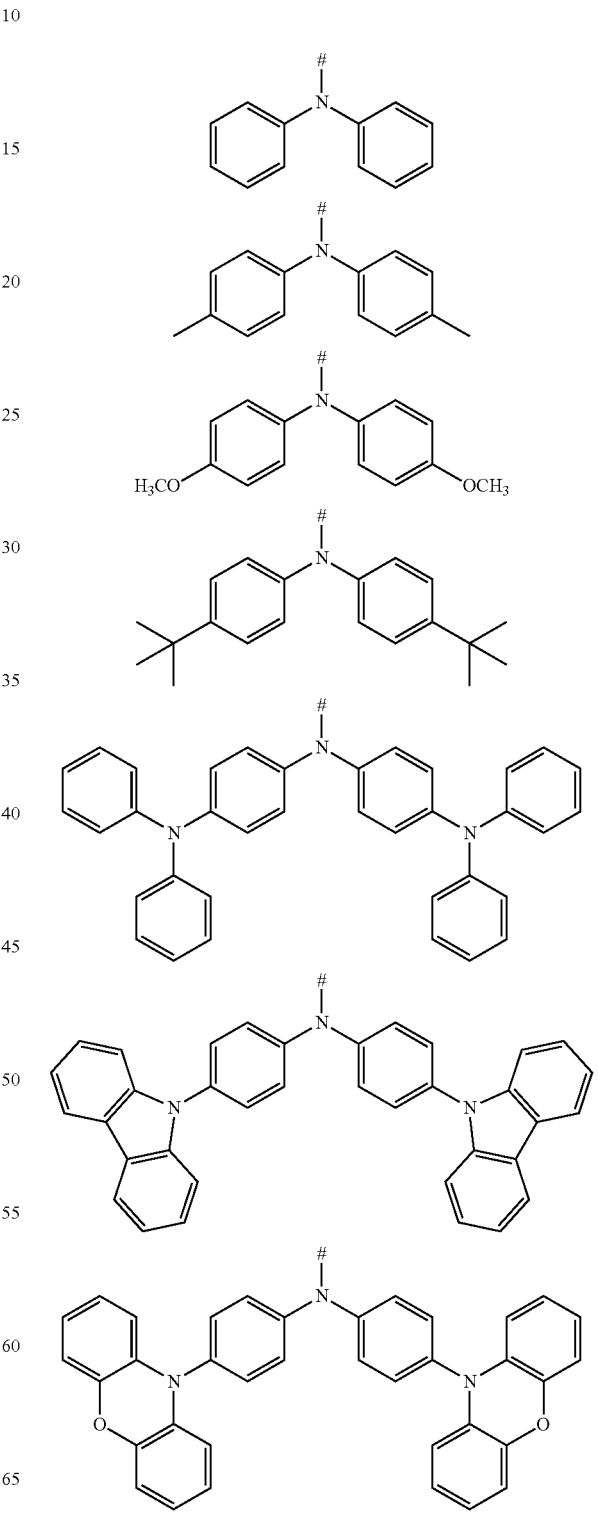

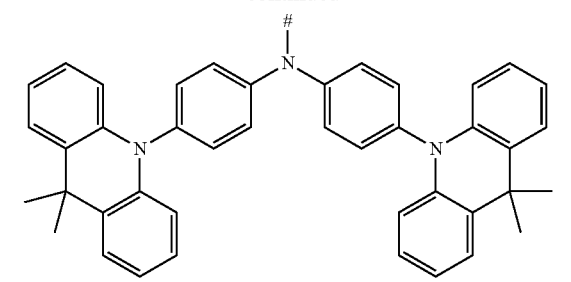

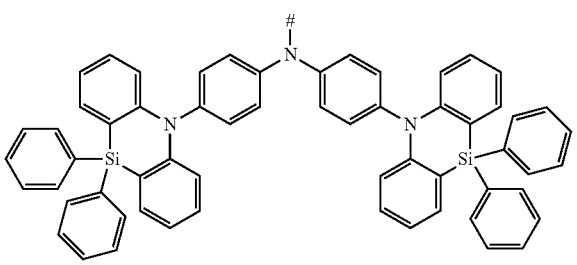

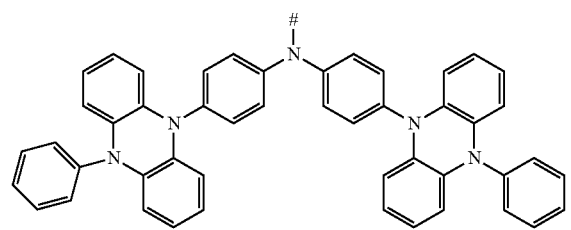

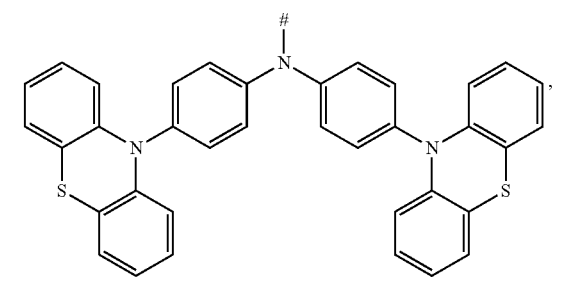

in which # indicates a bonding position to the Formula (1)

According to an embodiment of the compound of the present disclosure, the electron-donating group is according to any one of the following formulas:

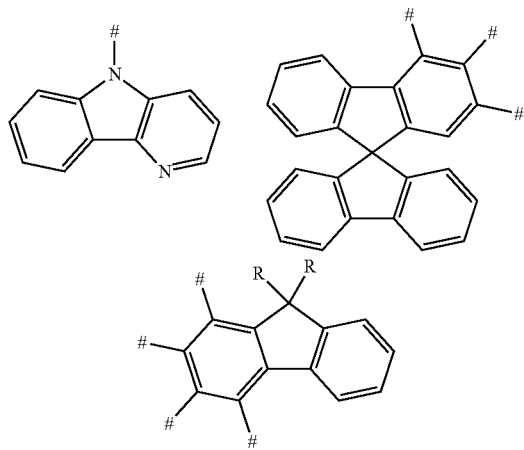

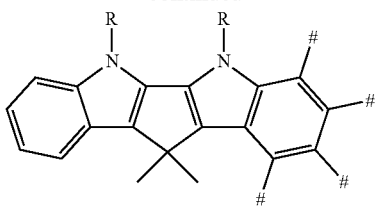

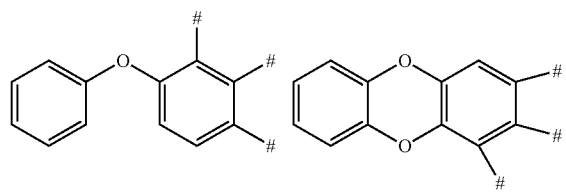

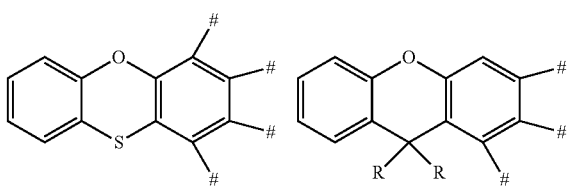

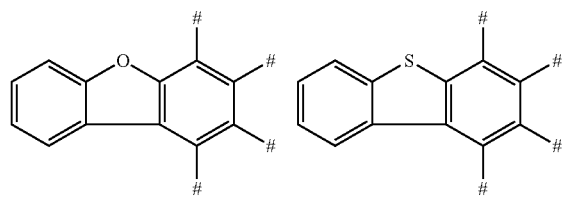

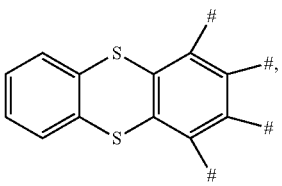

in which # indicates a bonding position to the Formula (1).

According to an embodiment of the compound of the present disclosure, the compound is selected from the following compounds:

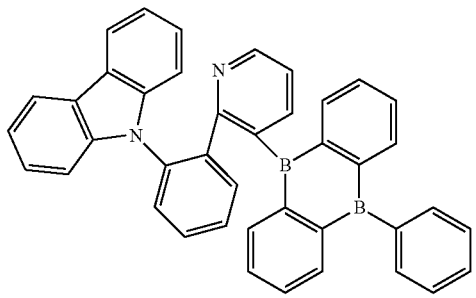

P1

-continued
P2
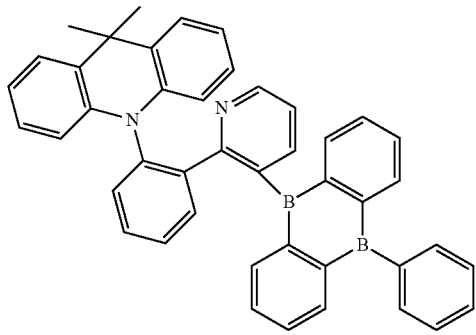
P3
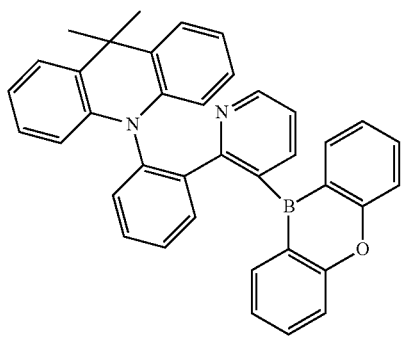
P4
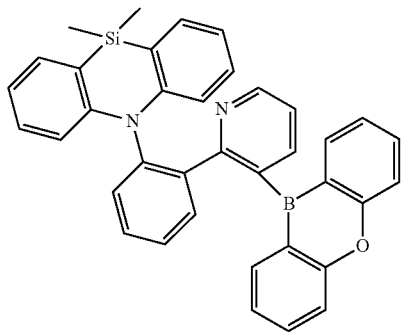
P5
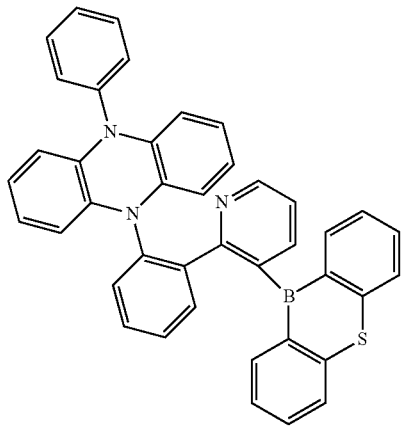
P6
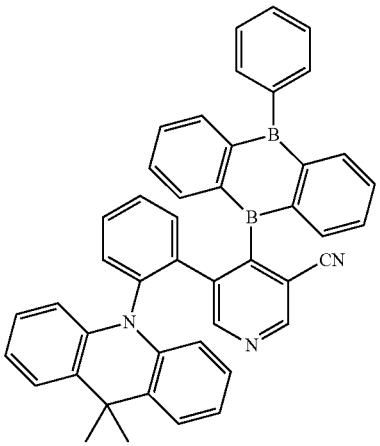
P7
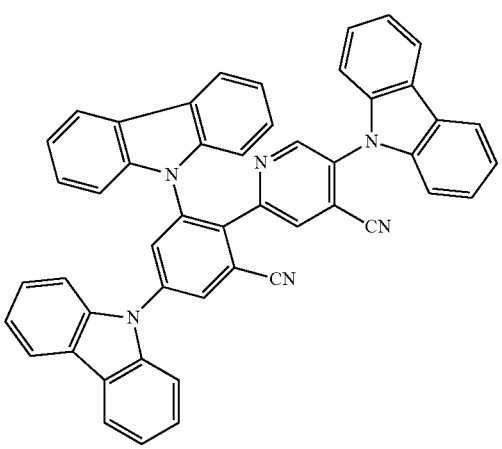
P8
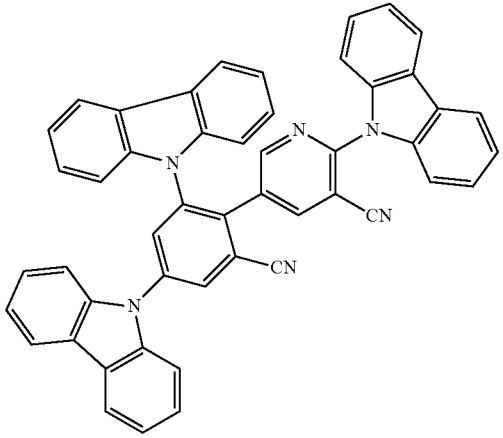

-continued
P9
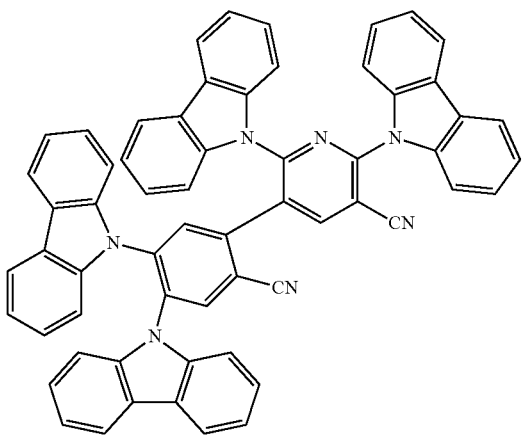
P10
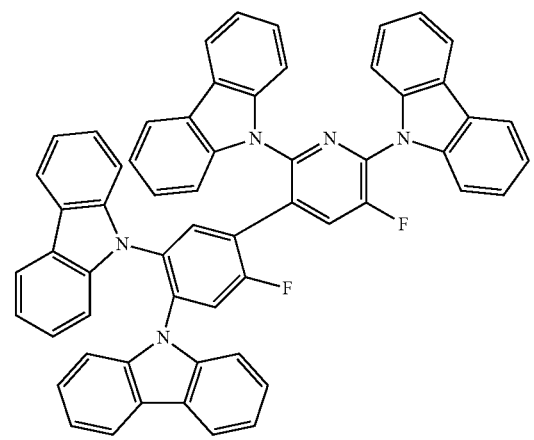
P11
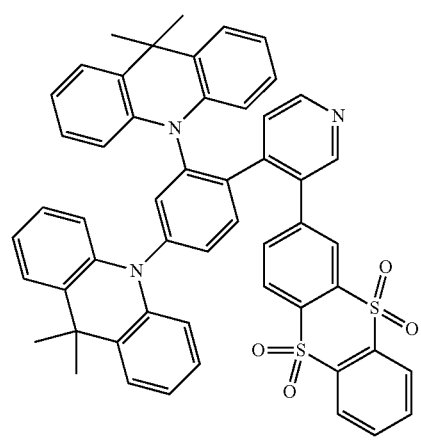
-continued
P12
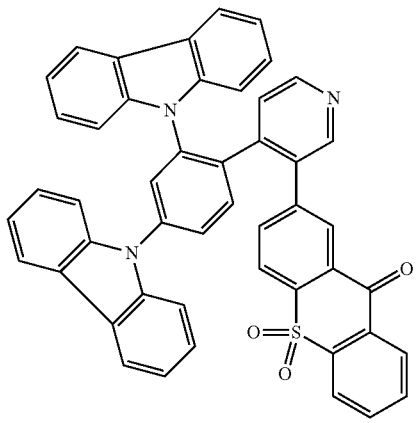
P13
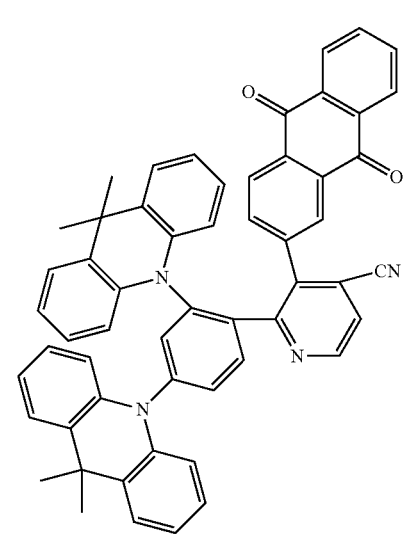
P14
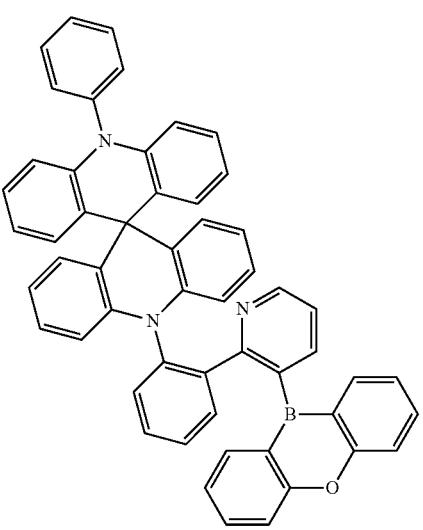

P15
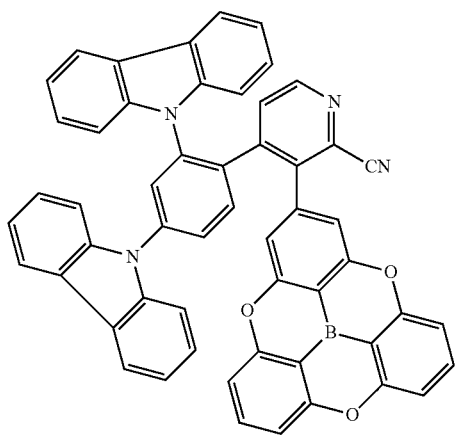
P16
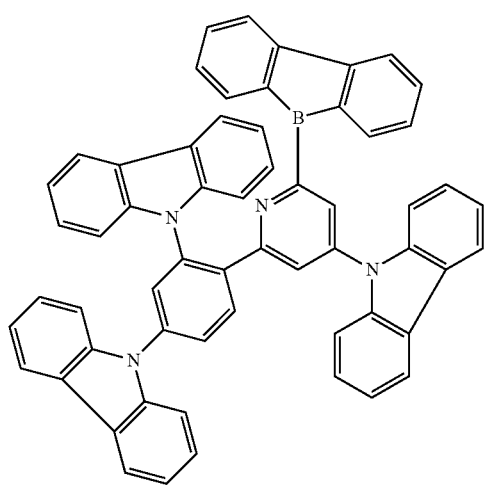
P17
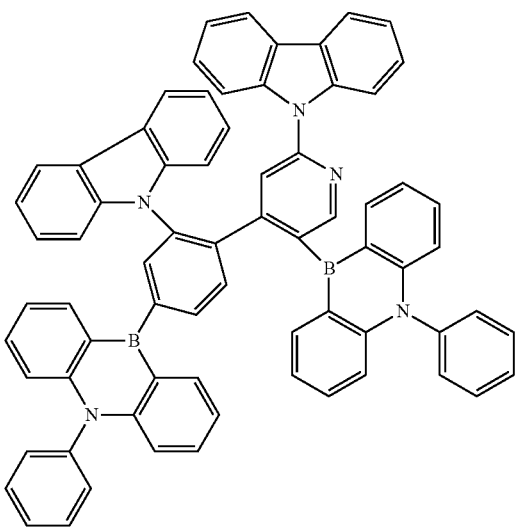
P18
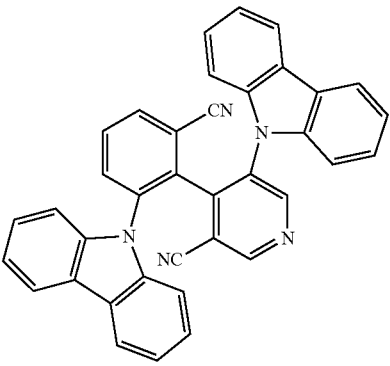
P19
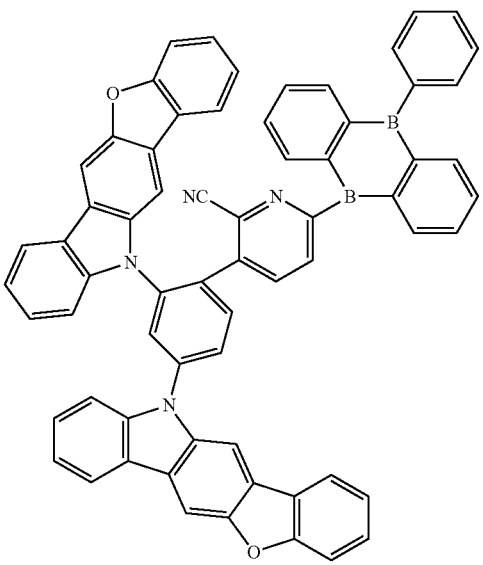
P20

P21
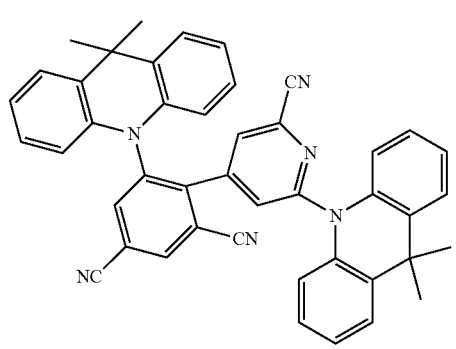
P22
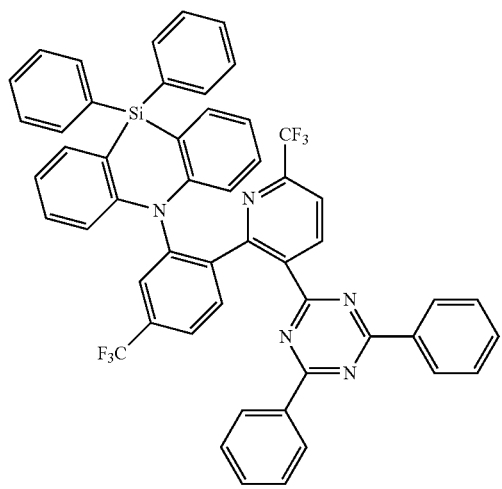
P23
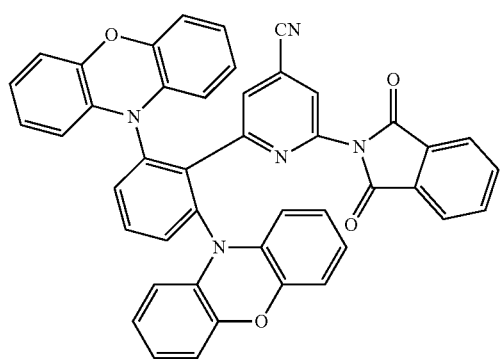
P24
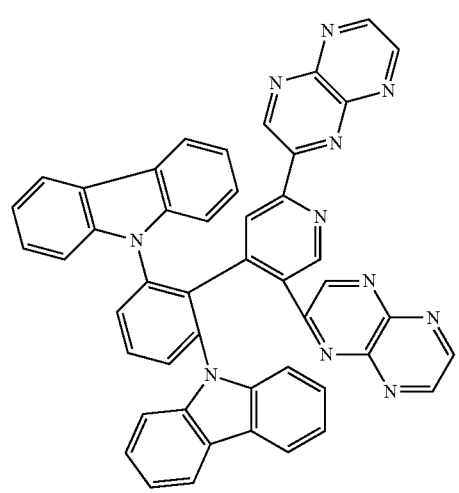
P25
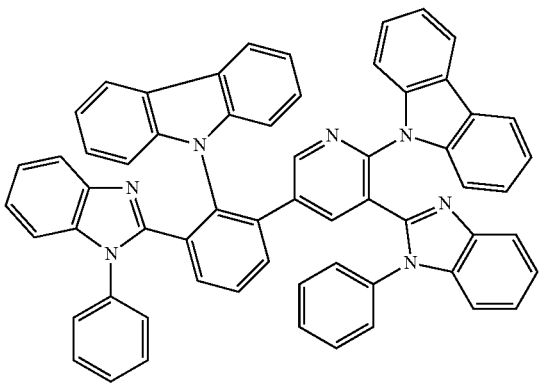
P26
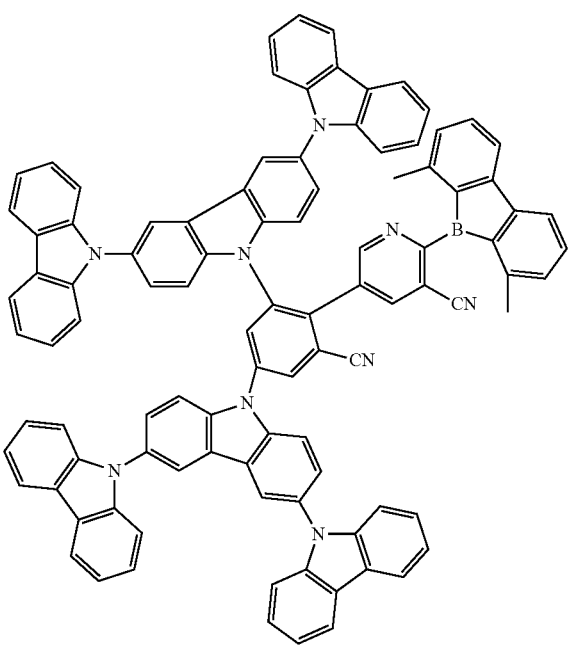

P27

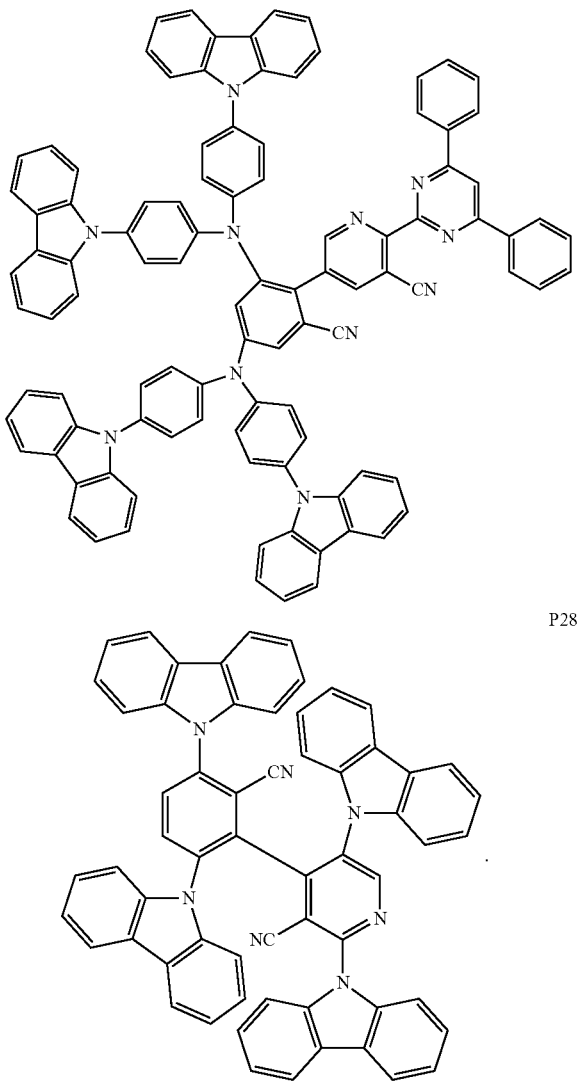

P28

According to an embodiment of the compound of the present disclosure, an energy level difference $\Delta E_{st}$ between a lowest singlet energy level S1 of the compound and a lowest triplet energy level T1 of the compound satisfies an equation $\Delta E_{st}=E_{S1}-E_{T1}\leq 0.30$ eV.

The compound of the present disclosure has the D-A type molecular structure, which is advantageous for achieving the effective separation of HOMO and LUMO. The adjacent connection between the electron-donating group and the electron-accepting group through benzene and six-membered heteroaryl ring can increase the dihedral angle between D unit and A unit, such that the steric hindrance between D unit and A unit is relatively larger to obtain a smaller $\Delta E_{st}$.

In addition, the structure of the compound according to the present disclosure can increase an intramolecular space-constraint effect, reduce the positive solvation discoloration effect of molecules, while improving the molecular luminescence color purity and achieving a smaller peak width at half height.

The compound of the present disclosure has a TADF property and is suitable for use as a host material and/or a guest material of an OLED light-emitting layer.

The present disclosure also provides methods for preparing the exemplary compounds P6, P12, P18, P25 and P28, as described in the Exemplary Synthesizing Examples 1-5 below.

Example 1

Synthesis of Compound P6

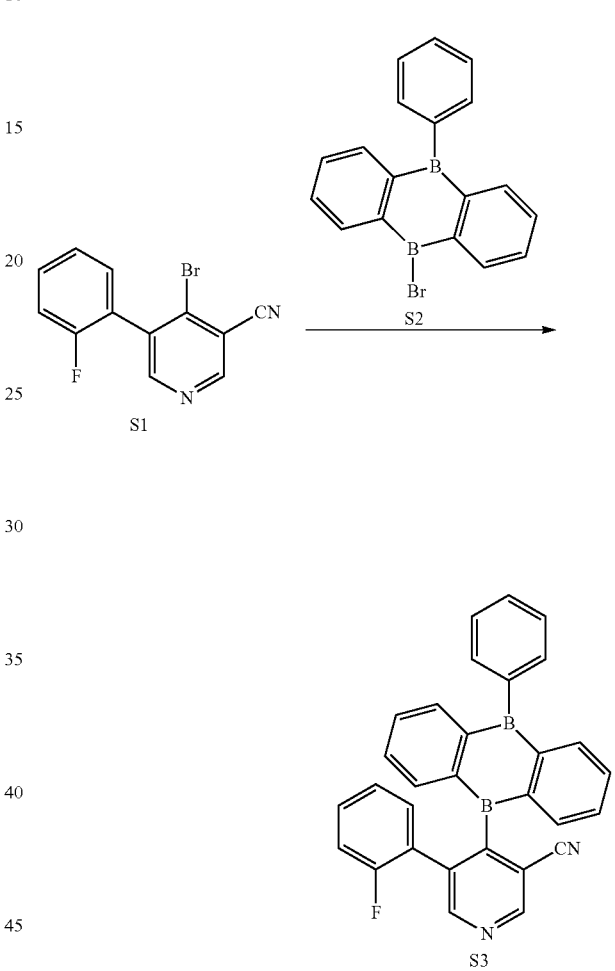

S1 (1.5 mmol) was dissolved in diethyl ether (40 mL) at −78° C., and an n-hexane solution of nBuLi (2.2 mmol) was added dropwise thereto. The reaction solution was continually stirred for 2 h, then slowly warmed to room temperature, and stirred at room temperature for 1 h. The reaction solution was again cooled to −78° C., and 25 mL of a toluene solution of S2 (1.6 mmol) was added dropwise while stirring. The reaction solution was slowly warmed to room temperature and stirred overnight. All solvents were removed by evaporation under reduced pressure, and a crude product was collected. The crude product was washed with methanol (3×30 mL) and pentane (3×30 mL), and the crude product was collected again. The crude product was purified by silica gel chromatography, in which a mixture of n-hexane:trichloromethane (5:1) was used as an eluent, and finally purified to obtain a solid S3 (1.23 mmol, 78%).

MALDI-TOF MS: m/z calcd for $C_{30}H_{19}B_2FN_2$: 448.2. found: 448.5.

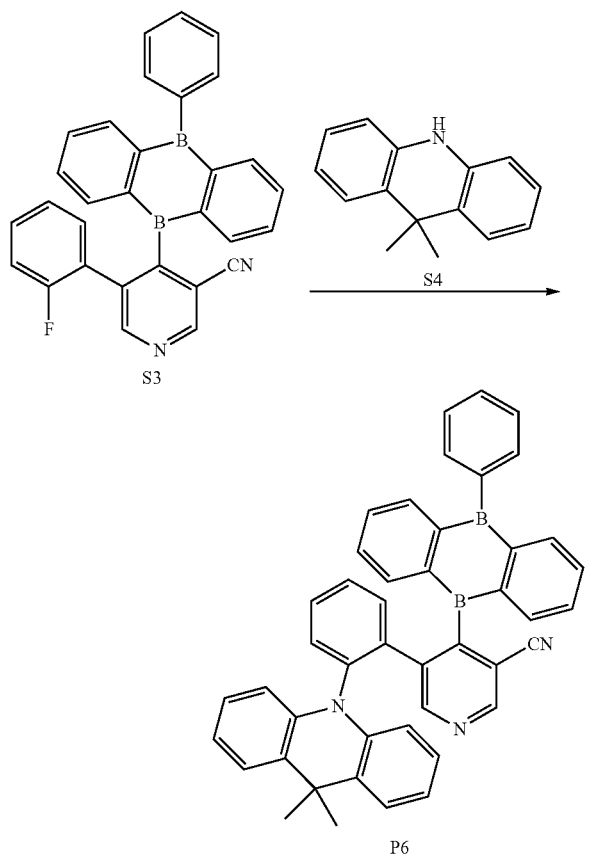

Under a protection of nitrogen atmosphere, Compound S3 (2.5 mmol) was weighed and added into a 250 mL two-necked flask, and 60 mL of dry anhydrous tetrahydrofuran was added to dissolve the Compound S3. NaH (stored in 60% oil, 3.0 mmol) was washed three times with n-hexane, added to the two-necked flask, and stirred for 30 min. Then, S2 (2.75 mmol) was added into the two-necked flask, and the mixture was stirred at room temperature overnight. The reaction was quenched with methanol and water, extracted with dichloromethane. Then, the organic phase was collected and dried with $Na_2SO_4$. The dried solution was filtered, the solvent was removed on a rotary evaporator to obtain a crude product. The crude product was purified by silica gel chromatography, and then purified by sublimation to obtain a solid P6 (1.8 mmol, 74%).

MALDI-TOF MS: m/z calcd for $C_{45}H_{33}B_2N_3$: 637.3. found: 637.4.

Elemental analysis: calcd: C, 84.80; H, 5.22; B, 3.39; N, 6.59. found: C, 84.83; H, 5.24; B, 3.37; N, 6.56.

Example 2

Synthesis of Compound P12

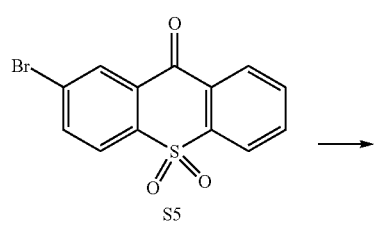

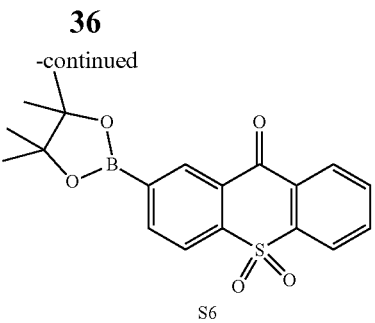

S5 (7.5 mmol), Bis(pinacolato)diboron (8.5 mmol), (1,1'-bis(diphenylphosphino)ferrocene) dichloropalladium (II) (0.1 mmol) and potassium acetate (20 mmol) were added into a 250 ml three-necked flask, separately, and the degassing and nitrogen displacement were quickly repeated 3 times while stirring. Then, 25 mL of tetrahydrofuran was added by a syringe. While stirring at a certain rotation speed, the obtained mixed solution reactants were heated to reflux at a reaction temperature of 80° C. for 5 h, and it was cooled to room temperature after the reaction was completed, then 25 ml of water was added thereto, and extracted with ethyl ether. The obtained organic phase was dried with anhydrous sodium sulfate, the solvent was evaporated, and purified by using column chromatography to obtain an intermediate S6 (6.2 mmol, 83%).

MALDI-TOF MS: m/z calcd for $C_{19}H_{19}BO_5S$: 370.1. found: 370.5.

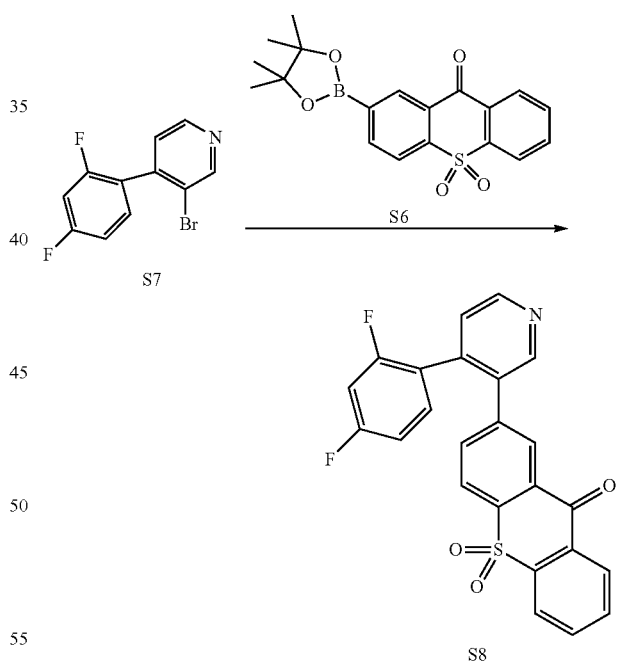

Under a protection of nitrogen atmosphere, Compound S7 (1.5 mmol), S10 (1.6 mmol), $[Pd_2(dba)_3]\cdot CHCl_3$ (0.05 mmol), and $HP(tBu)_3\cdot BF_4$ (0.1 mmol) were weighed and added into a 100 mL two-necked flask. 30 mL of toluene (pre-introducing $N_2$ for 15 min to remove oxygen) was added into the two-necked flask, then 2.5 mL of 1M aqueous solution of $K_2CO_3$ (pre-introducing $N_2$ for 15 min to remove oxygen) was added dropwise, and the mixture was stirred at room temperature overnight. After the reaction was completed, 20 mL of deionized water was added and a few drops of 2M HCl were added. The mixture was extracted with dichloromethane, the organic phase was collected and dried over anhydrous Na$_2$SO$_4$. The dried solution was filtered, and the solvent was removed on a rotary evaporator to obtain a crude product. The crude product was purified by silica gel chromatography to obtain a solid P8 (1.1 mmol, 73%).

MALDI-TOF MS: m/z calcd for C$_{24}$H$_{13}$F$_2$NO$_3$S: 433.1. found: 433.2.

MALDI-TOF MS: m/z calcd for C$_{48}$H$_{29}$N$_3$O$_3$S: 727.2. found: 727.5.

Elemental analysis: calcd for C, 79.21; H, 4.02; N, 5.77; O, 6.59; S, 4.41. found: C, 79.25; H, 4.04; N, 5.75; O, 6.57; S, 4.39.

Example 3

Synthesis of Compound P18

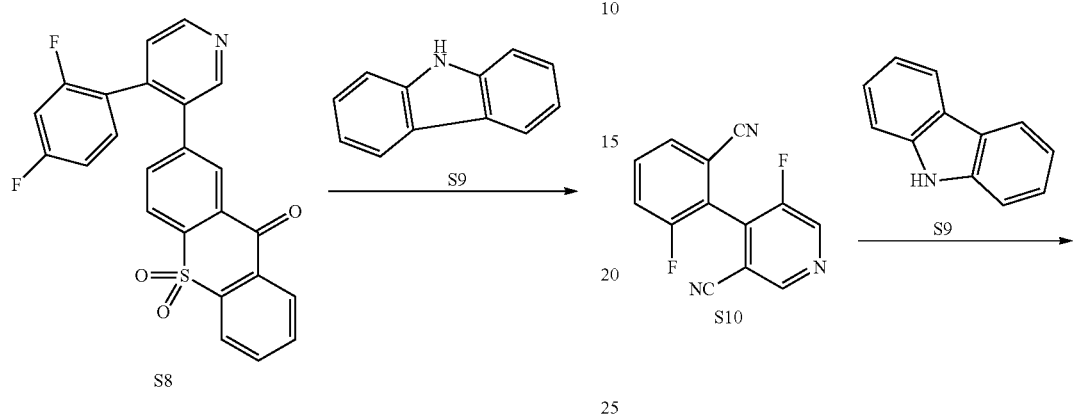

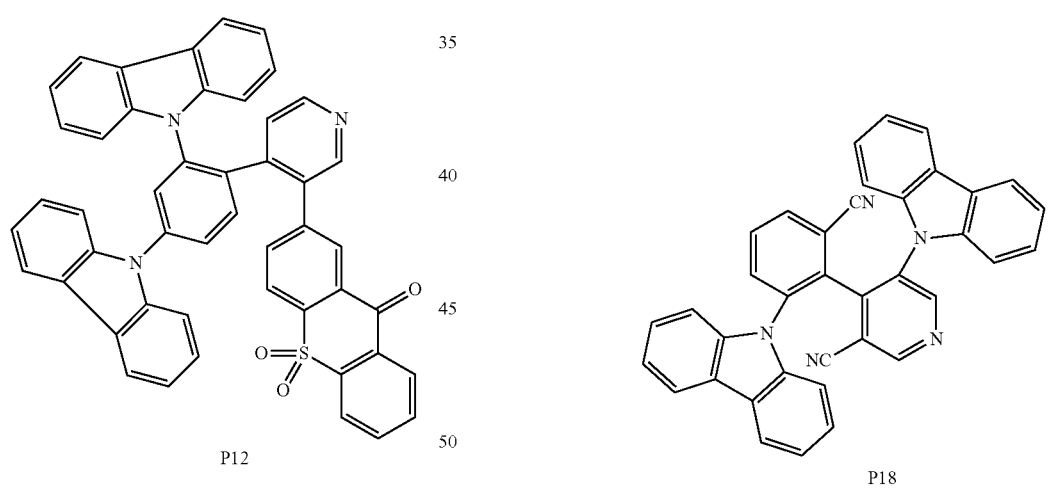

S8 (3.0 mmol), 9,9-dimethyl-9,10-dihydroacridine S2 (6.2 mmol), (dibenzylideneacetone) dipalladium (0) (0.12 mmol), sodium tert-butoxide (8.4 mmol), tetrafluoro tri-tert-butylphosphonium borate (0.2 mmol) were added into a 250 ml three-necked flask. The degassing and nitrogen displacement were quickly repeated 3 times while stirring, and then 100 mL of toluene was added by a syringe. The mixture was heated to reflux for 3 h under a stream of nitrogen. After the reaction was completed, the reaction solution cooled to room temperature was added with water, extracted with dichloromethane, and washed with saturated brine. After the organic phase was dried over anhydrous sodium sulfate, the solvent was removed by evaporation and purified by column chromatography to obtain a Compound P12 (2.0 mmol, 67%).

S10 (1.8 mmol), S9 (3.8 mmol), (dibenzylideneacetone) dipalladium (0) (0.08 mmol), sodium t-butoxide (6.4 mmol), tri-tert-butylphosphonium tetrafluoroborate (0.16 mmol) were added into a 250 ml three-necked flask. The degassing and nitrogen displacement were quickly repeated 3 times while stirring, and then 50 mL of toluene was added by a syringe. The mixture was heated to reflux for 3 h under a stream of nitrogen. After the reaction was completed, the reaction solution cooled to room temperature was added with water, extracted with dichloromethane, and washed with saturated brine. The organic phase was dried over anhydrous sodium sulfate, the solvent was removed by evaporation and purified by column chromatography to obtain a Compound P18 (1.1 mmol, 63%).

MALDI-TOF MS: m/z calcd for $C_{37}H_{21}N_5$: 535.2. found: 535.4.

Elemental analysis: calcd for C, 82.97; H, 3.95; N, 13.08. found: C, 82.99; H, 3.96; N, 13.05.

Example 4

Synthesis of Compound P25

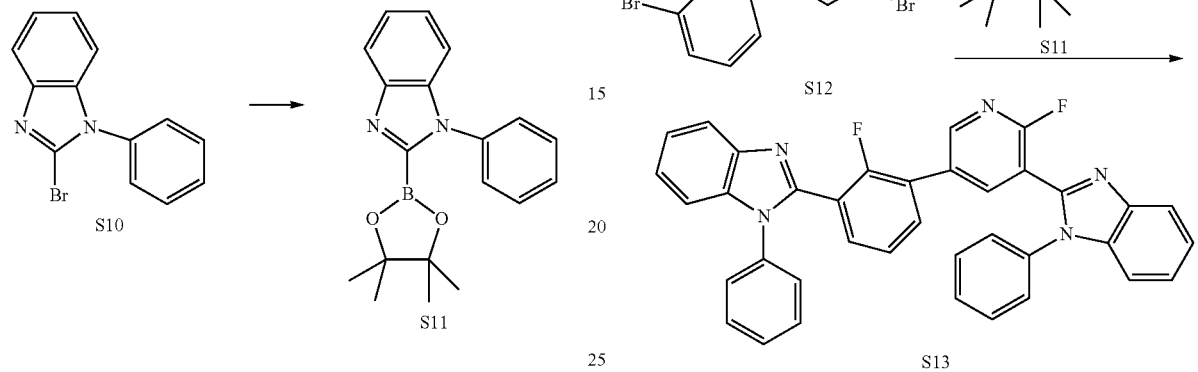

S10 (4.5 mmol), Bis(pinacolato)diboron (5.2 mmol), (1,1'-bis(diphenylphosphino)ferrocene) dichloropalladium (II) (0.1 mmol) and potassium acetate (20 mmol) were added into a 250 ml three-necked flask. The degassing and nitrogen displacement were quickly repeated 3 times while stirring, and then 45 mL of tetrahydrofuran was added by a syringe. While stirring at a certain rotation speed, the obtained mixed solution reactant was heated to reflux at a reaction temperature of 80° C. for 5 h. After the reaction was completed, the reaction solution was cooled to room temperature and added with 25 mL of water, and extracted with ethyl ether. The organic phase was dried over anhydrous sodium sulfate, the solvent was removed by evaporation and purified by column chromatography to obtain an intermediate S11 (3.7 mmol, 82%).

MALDI-TOF MS: $C_{19}H_{21}BN_2O_2$, m/z calcd: 320.2. found: 320.5.

Under a protection of nitrogen atmosphere, Compound S12 (1.5 mmol), 511 (3.2 mmol), [Pd$_2$(dba)$_3$].CHCl$_3$ (0.1 mmol), and HP(tBu)$_3$.BF4 (0.2 mmol) were weighed and added into a 250 mL two-necked flask. 100 mL of toluene (pre-introducing N$_2$ for 15 min to remove oxygen) was added into the two-necked flask, then 3.0 mL of 1M aqueous solution of K$_2$CO$_3$ (pre-introducing N$_2$ for 15 min to remove oxygen) was added dropwise, and the mixture was stirred at room temperature overnight. After the reaction was completed, 50 mL of deionized water was added and a few drops of 2M HCl were added. The mixture was extracted with dichloromethane, the organic phase was collected and dried over anhydrous Na$_2$SO$_4$. The dried solution was filtered, and the solvent was removed on a rotary evaporator to obtain a crude product. The crude product was purified by silica gel chromatography to obtain a solid S13 (1.0 mmol, 67%).

MALDI-TOF MS: m/z calcd for $C_{37}H_{23}F_2N_5$: 575.2. found: 575.4.

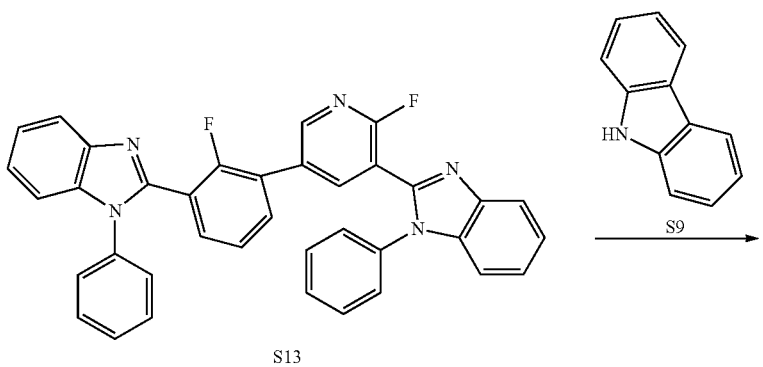

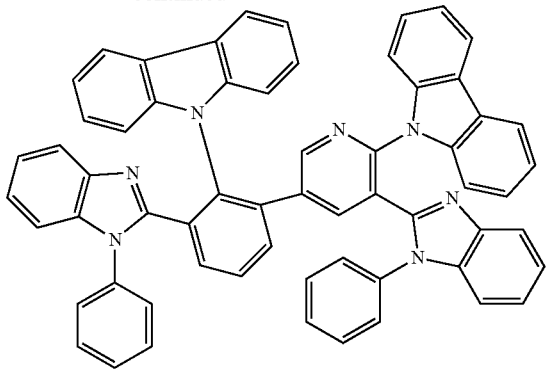

P25

S13 (2.25 mmol), S9 (4.75 mmol), (dibenzylideneacetone) dipalladium (0) (0.12 mmol), sodium t-butoxide (8.0 mmol), tri-tert-butylphosphonium tetrafluoroborate (0.24 mmol) were added into a 250 ml three-necked flask. The degassing and nitrogen displacement were quickly repeated 3 times while stirring, and then 100 mL of toluene was added by a syringe. The mixture was heated to reflux for 3 h under a stream of nitrogen. After the reaction was completed, the reaction solution cooled to room temperature was added with water, extracted with dichloromethane, and washed with saturated brine. The organic phase was dried over anhydrous sodium sulfate, the solvent was removed by evaporation and purified by column chromatography to obtain a Compound P25 (1.1 mmol, 63%).

MALDI-TOF MS: m/z calcd for $C_{61}H_{39}N_7$: 869.3. found: 869.5.

Elemental analysis: calcd for C, 84.21; H, 4.52; N, 11.27. found: C, 84.25; H, 4.50; N, 11.25.

Example 5

Synthesis of Compound P28

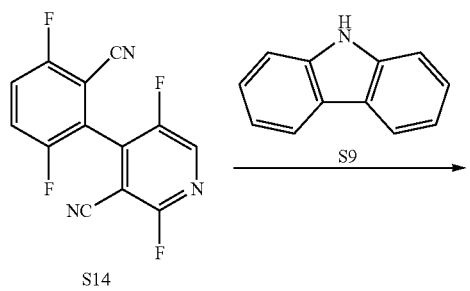

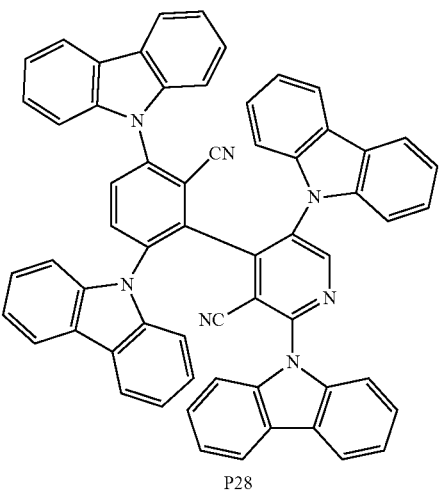

P28

S14 (1.5 mmol), S9 (6.3 mmol), (dibenzylideneacetone) dipalladium (0) (0.24 mmol), sodium t-butoxide (16.0 mmol), tri-tert-butylphosphonium tetrafluoroborate (0.48 mmol) were added into a 250 ml three-necked flask. The degassing and nitrogen displacement were quickly repeated 3 times while stirring, and then 100 mL of toluene was added by a syringe. The mixture was heated to reflux for 3 h under a stream of nitrogen. After the reaction was completed, the reaction solution cooled to room temperature was added with water, extracted with dichloromethane, and washed with saturated brine. The organic phase was dried over anhydrous sodium sulfate, the solvent was removed by evaporation and purified by column chromatography to obtain a Compound P28 (0.87 mmol, 58%).

MALDI-TOF MS: m/z calcd for $C_{61}H_{35}N_7$: 865.3. found: 865.5.

Elemental analysis: calcd for C, 84.60; H, 4.07; N, 11.32. found: C, 84.64; H, 4.05; N, 11.30.

Compound Performance Tests
(1) Simulation Calculation of Compounds

TABLE 1

Parameter characterization of compounds

| | Compounds | HOMO (eV) | LUMO (eV) | $S_1$ (eV) | $T_1$ (eV) | $\Delta E_{ST}$ (eV) | $E_g$ (eV) |
|---|---|---|---|---|---|---|---|
| Example 1 | P6 | −5.50 | −3.03 | 2.71 | 2.62 | 0.09 | 2.47 |
| Example 2 | P12 | −5.73 | −2.82 | 2.92 | 2.84 | 0.08 | 2.91 |
| Example 3 | P18 | −6.02 | −2.62 | 3.14 | 2.97 | 0.17 | 3.4 |
| Example 4 | P25 | −5.68 | −2.35 | 2.92 | 2.78 | 0.14 | 3.33 |
| Example 5 | P28 | −5.83 | −2.71 | 2.97 | 2.78 | 0.19 | 3.12 |
| Comparative Example | CBP | −5.61 | −1.76 | 3.45 | 2.60 | 0.85 | 3.85 |

It can be seen from Table 1 that the/JEST of respective compound according to the present disclosure is smaller than 0.3 ev, which means a small difference between the singlet energy level and the triplet energy level, and thus the compounds are suitable to be used as the TADF materials. In Table 1, $S_1$ represents a singlet energy level, $T_1$ represents a triplet energy level, $\Delta E_{ST}$ represents an energy level difference between the singlet energy level and the triplet energy level, and $E_g$ represents an energy level difference between HOMO and LUMO energy levels.

The present disclosure further provides a display panel, and the display panel includes an organic light-emitting display device. The organic light-emitting display device includes an anode, a cathode, and a light-emitting layer disposed between the anode and the cathode. A light-emitting material of the light-emitting layer includes one or more of the compounds according to the present disclosure.

In an embodiment of the display panel according to the present disclosure, the light-emitting layer includes a host material and a guest material. The host material is any one or more selected from the group consisting of 2,8-bis(diphenylphosphinyl)dibenzothiophene, 4,4'-bis(9-carbazolyl)biphenyl, 3,3'-bis(N-carbazolyl)-1,1'-biphenyl, 2,8-bis(diphenylphosphinyl)dibenzofuran, bis(4-(9H-carbazolyl-9-yl)phenyl)diphenylsilane, 9-(4-tert-butylphenyl)-3,6-bis(triphenylsilyl)-9H-carbazole, bis(2-diphenylphosphinyl)diphenyl ether, 1,3-bis[3,5-di(pyridine-3-yl)phenyl]benzene, 4,6-bis(3,5-di(3-pyridyl)phenyl)-2-methylpyrimidine, 9-(3-(9H-carbazolyl-9-yl)phenyl)-9H-carbazole-3-cyano, 9-phenyl-9-[4-(triphenylsilyl)phenyl]-9H-fluorene, 1,3,5-tris(1-phenyl-1H-benzoimidazol-2-yl)benzene, diphenyl[4-(triphenylsilyl)phenyl]phosphine oxide, 4,4',4"-tris(carbazol-9-yl)triphenylamine, 2,6-dicarbazolyl-1,5-pyridine, polyvinylcarbazole, polyfluorene, and combinations thereof. The guest material is one or more selected from the group consisting of the compounds according to the present disclosure, and combinations thereof. An energy level difference between a HOMO energy level of the host material and a HOMO energy level of the guest material is smaller than 0.6 eV, or an energy level difference between LUMO energy level of the host material and LUMO energy level of the guest material is smaller than 0.6 eV.

In an embodiment of the display panel according to the present disclosure, the light-emitting material of the light-emitting layer includes a host material and a guest material, the host material is one or more selected from the group consisting of the compounds according to the present disclosure, and combinations thereof. The guest material is selected from the group consisting of fluorescent material, thermally activated delayed fluorescent material, and phosphorescent material. An energy level difference between a HOMO energy level of the host material and a HOMO energy level of the guest material is smaller than 0.6 eV, or an energy level difference between a LUMO energy level of the host material and a LUMO energy level of the guest material is smaller than 0.6 eV.

In an embodiment of the display panel according to the present disclosure, the light-emitting material of the light-emitting layer includes a host material and a guest material, the host material is one or more selected from the group consisting of the compounds according to the present disclosure, and combinations thereof, and the guest material is a fluorescent material or a thermally activated delayed fluorescent material. A singlet energy level of the guest material is smaller than singlet energy level of the host material, and a difference between the singlet energy level of the host material and the singlet energy level of the guest material is smaller than 1.0 eV.

In an embodiment of the display panel according to the present disclosure, the light-emitting material of the light-emitting layer includes a host material and a guest material, the host material is selected from the group consisting of the compounds according to the present disclosure, and combinations thereof, and the guest material is a phosphorescent material. A triplet energy level of the guest material is lower than a triplet energy level of the host material, and an energy level difference between the triplet energy level of the host material and the triplet energy level of the guest material is smaller than 1.0 eV.

According to an embodiment of the display panel of the present disclosure, the light-emitting layer includes a red light-emitting layer, and the host material is a red host material.

According to an embodiment of the display panel of the present disclosure, the light-emitting layer includes a green light-emitting layer, and the host material is a green host material.

According to an embodiment of the display panel of the present disclosure, the organic light-emitting device further includes one or more of a hole injection layer, a hole transmission layer, an electron blocking layer, a hole blocking layer, an electron transmission layer, and an electron injection layer.

The hole injection layer, the hole transmission layer, and the electron blocking layer are each made of a material selected from the group consisting of 2,2'-dimethyl-N,N-bis(1-naphthyl)-N,N-diphenyl[1,1'-biphenyl]-4,4'-diamine (α-NPD), 4,4',4"-tris(carbazol-9-yl)-triphenylamine (TCTA), 1,3-dicarbazole-9-yl benzene (mCP), 4, 4'-bis(9-carbazole)biphenyl (CBP), 3,3'-bis(N-carbazolyl)-1,1'-biphenyl (mCBP), 2,3,6,7,10,11-hexacyano-1,4,5,8,9,12- hexaazatriphenylene (HATCN), 4,4'-cyclohexylidenebis[N,N-bis(4-methylphenyl)aniline] (TAPC), N,N'-diphenyl-N,N'-(1-naphthyl)-1, 1'-biphenyl-4,4'-diamine (α-NPB), N,N'-bis (naphthalen-2-yl)-N,N'-di(phenyl)biphenyl-4,4'-diamine (NPB), poly(3,4-ethylenedioxythiophene)-polystyrenesulfonate (PEDOT:PSS), polyvinyl carbazole (PVK), 9-phenyl-3,9-bicarbazolyl (CCP), and molybdenum trioxide (MoO3). However, the material is not limited thereto.

The hole blocking layer, the electron transmission layer, and the electron injection layer are each made of a material selected from the group consisting of 2,8-bis(diphenylphosphinyl)dibenzothiophene (PPT), TSPO1, 1,3,5-tris(1-phenyl-1H-benzimidazol-2-yl)benzene (TPBi), 2,8-bis(diphenylphosphinyl)dibenzofuran (PPF), bis[2-(diphenylphosphino)phenyl] ether oxide (DPEPO), lithium fluoride (LiF), 4,6-bis(3,5-di-3-pyridylphenyl)-2-methylpyrimidine (B3PYMPM), 4,7-diphenyl-1,10-phenanthroline (Bphen), 1,3,5-tris[(3-pyridyl)-3-phenyl]benzene (TmPyBP), tris[2,4,6-trimethyl-3-(3-pyridyl)phenyl]borane (3TPYMB), 1,3-bis(3,5-dipyridine-3-yl-phenyll benzene (B3PYPB), 1,3-bis[3,5-di(pyridin-3-yl)phenyl]benzene (BMPYPHB), 2,4,6-Tris(biphenyl-3-yl)-1,3,5-triazine (T2T), diphenylbis(4-(pyridin-3-yl)phenyl)silane (DPPS), cesium carbonate ($Cs_2O_3$), bis(2-methyl-8-quinolinolato-N1,O8)-(1,1'-Biphenyl-4-olato)aluminum (BAlq), 8-hydroxyquinoline lithium (Liq), and tris(8-hydroxyquinoline) aluminum ($Alq_3$). However, the material is not limited thereto.

In the display panel according to the present disclosure, in an embodiment, the anode of the organic light-emitting device comprises a metal, such as a metal selected from the group consisting of copper, gold, silver, iron, chromium, nickel, manganese, palladium, platinum, and alloys thereof. In an embodiment, the anode comprises a metal oxide, such as a metal oxide selected from the group consisting of indium oxide, zinc oxide, indium tin oxide (ITO), indium zinc oxide (IZO), and combinations thereof. In an embodiment, the anode comprises a conductive polymer, such as a conductive polymer selected from the group consisting of polyaniline, polypyrrole, poly(3-methylthiophene) and and combinations thereof. In addition to the anode material mentioned above, the anode also can be made of any suitable material selected from the anode materials known in the related art, and combinations thereof, as long as the material of the anode is conductive to hole injection.

In the display panel according to the present disclosure, in an embodiment, the cathode of the organic light-emitting device comprises a metal, such as a metal selected from the group consisting of aluminum, magnesium, silver, indium, tin, titanium, and alloys thereof. In an embodiment, the cathode comprises a multiple-layer metal material, such as a multiple-layer metal material selected from the group consisting of LiF/Al, $LiO_2$/Al, $BaF_2$/Al, and combinations thereof. In addition to the cathode materials listed above, the cathode also can be made of any suitable material selected from the cathode material known in the related art, and combinations thereof, as long as the material of the cathode is conductive to electron injection.

The organic light-emitting display device can be manufactured by methods known in the related art, which are not described in detail herein. In the present disclosure, the organic light-emitting display device is manufactured by forming an anode on a transparent or opaque smooth substrate, forming an organic thin layer on the anode, and further forming a cathode on the organic thin layer. The organic thin layer can be formed by a known method such as vapor deposition, sputtering, spin coating, dipping, ion plating, and the like.

Figure 4:
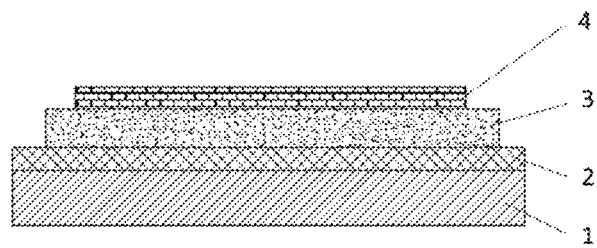
FIG. 4 is a structural schematic diagram of an OLED according to an embodiment of the present disclosure.

In an embodiment of the display panel of the present disclosure, the structure of the organic light-emitting device (OLED) is shown in FIG. 4, in which a substrate made of glass or other suitable material (such as plastic) is denoted with 1; a transparent anode such as ITO or IGZO is denoted with 2; an organic film layer (including a light-emitting layer) is denoted with 3; and a metal cathode is denoted with 4, which together constitute the whole OLED device.

Device Example 1

An exemplary device example is provided below for illustrating the practical application of the compound according to the present disclosure in an organic light-emitting display panel, in which the compound according to the present disclosure was used as a dopant material (guest material) in the light-emitting layer.

An anode substrate having an ITO film with a thickness of 100 nm was ultrasonically washed with distilled water, acetone, and isoinol, then dried in an oven, and the surface was subjected to UV treatment for 30 minutes. Then the substrate was transferred to a vacuum vapor deposition chamber. The vapor deposition of each layer was carried out under a vacuum of $2 \times 10^{-6}$ Pa. A hole injection layer was formed by depositing 5 nm of HATCN. A hole transmission layer (HTL) was formed by depositing 40 nm of N,N'-diphenyl-N,N'-bis(1-naphthyl)-1,1'biphenyl-4,4"diamine (α-NPB) and then depositing 10 nm of 4,4',4"-tris(carbazol-9-yl)-triphenylamine (TCTA). The target compound P6 according to the present disclosure used as a dopant of the light-emitting layer, and 3,3'-bis (N-carbazolyl)-1,1'-biphenyl (mCBP) used as a host material of the light-emitting layer, were deposited on the hole transmission layer at the same time, so as to form a light-emitting layer having a thickness of 30 nm. A hole blocking layer (HBL) having a thickness of 5 nm was deposited on the light-emitting layer with diphenyl [4-(triphenylsilyl) phenyl] phosphine oxide (TSPO1). An electron transmission layer (ETL) having a thickness of 30 nm was deposited on the hole blocking layer with 4,7-diphenyl-1,10-phenanthroline (Bphen). Then, a LiF layer having a thickness of 2.5 nm and an Al layer having a thickness of 100 nm were deposited on the electron transmission layer sequentially, serving as an electron injection layer (EIL) and a cathode, respectively, so as to obtain an organic light-emitting display device.

The organic electroluminescent device also can be manufactured by a solution method.

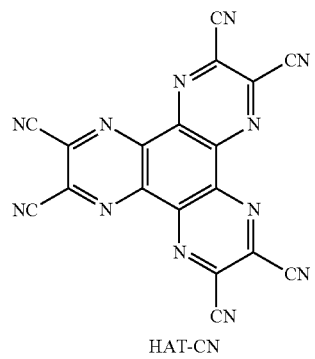
HAT-CN
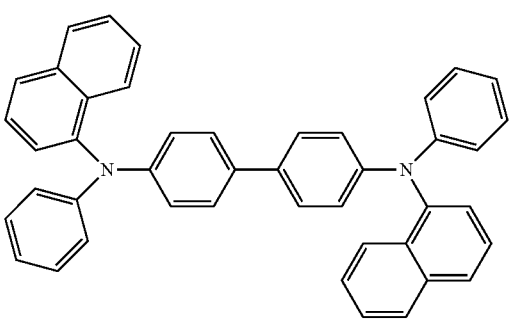
NPB
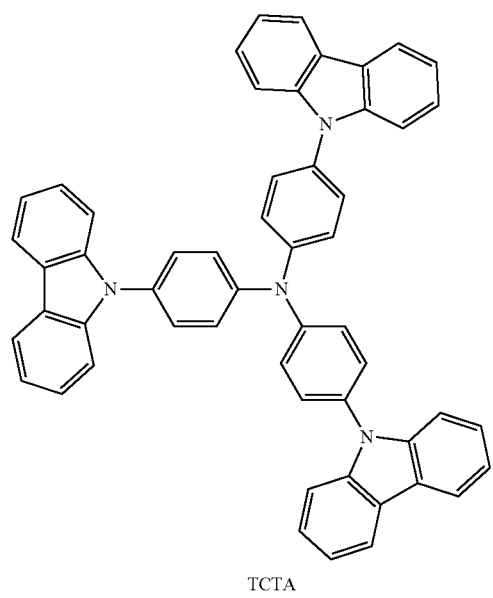
TCTA
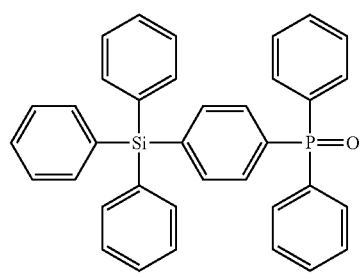
TSPO1
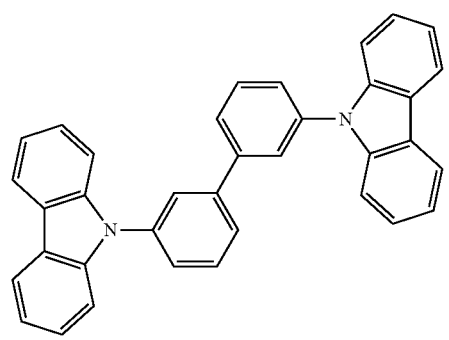
mCBP

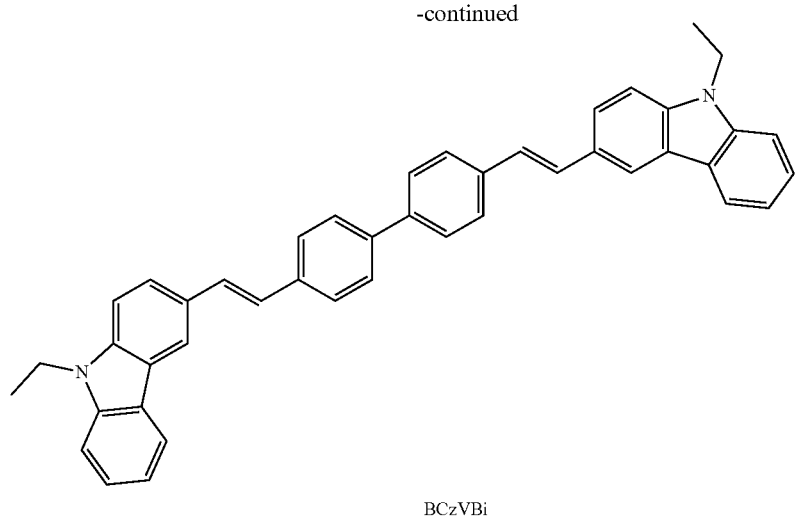

BCzVBi

Device Example 2

Device Example 2 differs from Device Example 1 in that Compound P6 was replaced with Compound P12. The other manufacturing steps are the same as those described in Device Example 1.

Device Example 3

Device Example 3 differs from Device Example 1 in that Compound P6 was replaced with Compound P18. The other manufacturing steps are the same as those described in Device Example 1.

Device Example 4

Device Example 4 differs from Device Example 1 in that Compound P6 was replaced with Compound P25. The other manufacturing steps are the same as those described in Device Example 1.

Device Example 5

Device Example 5 differs from Device Example 1 in that Compound P6 was replaced with Compound P28. The other manufacturing steps are the same as those described in Device Example 1.

Device Comparative Example 1

Device Comparative Example 1 differs from Device Example 1 in that Compound P6 was replaced with compound BCzVBi. The other manufacturing steps are the same as those described in Device Example 1.

TABLE 2

| No. | Guest material | Driving voltage (V) | EQE /% | CE (cd/A) | Color |
|---|---|---|---|---|---|
| Device Example 1 | P6 | 4.26 | 13.2 | 19.8 | Blue light |
| Device Example 2 | P12 | 4.08 | 12.4 | 19.2 | Blue light |
| Device Example 3 | P18 | 4.15 | 9.8 | 16.2 | Blue light |
| Device Example 4 | P25 | 3.98 | 10.7 | 17.4 | Blue light |
| Device Example 5 | P28 | 4.04 | 10.4 | 17.0 | Blue light |
| Device Comparative Example 1 | BCzVBi | 4.82 | 4.8 | 7.5 | Blue light |

It can be seen from Table 2 that, the organic light-emitting devices respectively adopting Compounds P6, P12, P18, P25 and P28 as dopant (host material) have each a significantly higher $EQE_{(max)}$ than the Device Comparative Example 1 in which the classic blue light-emitting material BCzVBi was used as the fluorescent dopant. This is mainly attributed to the properties of TADF of Compounds P6, P12, P18, P25 and P28 themselves. The triplet excitons, which forbid the transition of the traditional fluorescent molecules (such as BCzVBi), are utilized to emit light, thereby improving device efficiency.

Device Example 6

An exemplary device example is provided below for illustrating the practical application of the compound according to the present disclosure in an organic light-emitting display panel, in which the compound according to the present disclosure was used as a host material of a light-emitting layer, and a fluorescent material or a phosphorescent material was used as a dopant.

An anode substrate having an ITO film with a thickness of 100 nm was ultrasonically washed with distilled water, acetone, and isoinol, then dried in an oven, and the surface was subjected to UV treatment for 30 minutes. Then the substrate was transferred to a vacuum vapor deposition chamber. The vapor deposition of each layer was carried out under a vacuum of $2\times10^{-6}$ Pa. A hole injection layer was formed by depositing 5 nm of HATCN. A hole transmission layer (HTL) was formed by depositing 40 nm of 2,2'-dimethyl-N,N'-bis(1-naphthyl)-N,N-diphenyl[1,1'-biphenyl]-4,4'-diamine (α-NPD) and then depositing 10 nm of 4,4',4''-tris(carbazol-9-yl)-triphenylamine (TCTA). The target Compound P6 according to the present disclosure used as a host material of the light-emitting layer, and Ir(ppy)$_3$ used as a dopant of the light-emitting layer, were deposited on the hole transmission layer at the same time, so as to form a light-emitting layer having a thickness of 30 nm. A hole blocking layer (HBL) having a thickness of 5 nm was deposited on the light-emitting layer with 1,3,5-tris(1-phenyl-1H-benzimidazol-2-yl)benzene (TPBi). An electron transmission layer (ETL) having a thickness of 30 nm was deposited on the hole blocking layer with 1,3,5-tris[(3-pyridyl)-3-phenyl]benzene (TmPyBP). Then, a LiF layer having a thickness of 2.5 nm and an Al layer having a thickness of 100 nm were deposited on the electron transmission layer sequentially, serving as an electron injection layer (EIL) and a cathode respectively, so as to obtain an organic light-emitting display device.

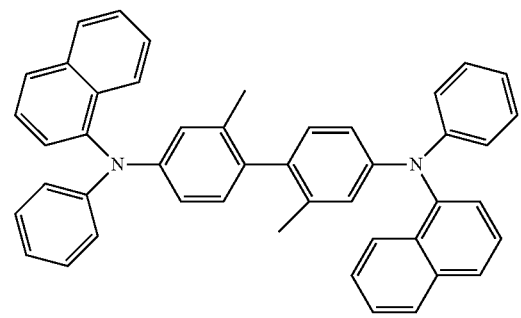

α-NPD

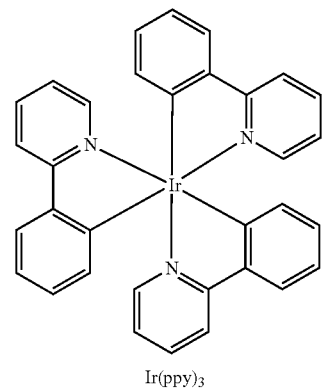

Ir(ppy)$_3$

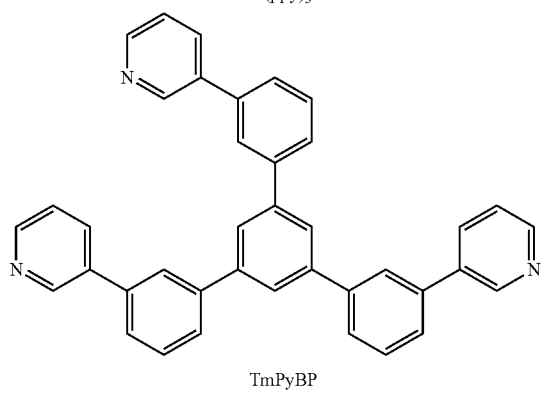

TmPyBP

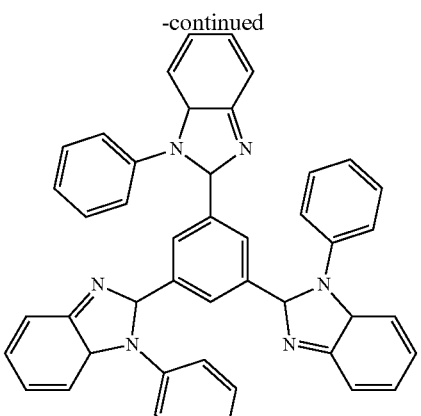

TPBI

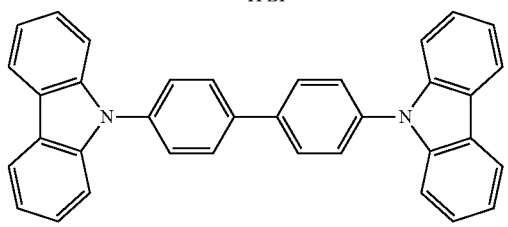

CBP

Device Example 7

Device Example 7 differs from Device Example 6 in that Compound P6 was replaced with Compound P12. The other manufacturing steps are the same as those described in Device Example 6.

Device Example 8

Device Example 8 differs from Device Example 6 in that Compound P6 was replaced with Compound P18. The other manufacturing steps are the same as those described in Device Example 6.

Device Example 9

Device Example 9 differs from Device Example 6 in that Compound P6 was replaced with Compound P25. The other manufacturing steps are the same as those described in Device Example 6.

Device Example 10

Device Example 10 differs from Device Example 6 in that Compound P6 was replaced with Compound P28. The other manufacturing steps are the same as those described in Device Example 6.

Device Comparative Example 2

Device Comparative Example 2 differs from Device Example 6 in that Compound P6 was replaced with compound CBP. The other manufacturing steps are the same as those described in Device Example 6.

TABLE 3

Parameter characterization of devices

| No. | Host material | Driving voltage (V) | EQE /% | CE (cd/A) |
|---|---|---|---|---|
| Device Example 6 | P6 | 4.05 | 16.0 | 26.2 |
| Device Example 7 | P12 | 3.98 | 15.8 | 25.5 |
| Device Example 8 | P18 | 4.02 | 14.6 | 24.2 |
| Device Example 9 | P25 | 4.08 | 15.2 | 24.9 |
| Device Example 10 | P28 | 4.10 | 14.8 | 25.0 |
| Device Comparative Example 2 | CBP | 4.16 | 12.8 | 20.6 |

By using the Compounds P6, P12, P18, P25 and P28 according to the present disclosure as the host material respectively, and using Ir(ppy)3 as the dopant, the doped devices achieve the maximum external quantum efficiency of 16.0%, indicating that the compounds of the present invention can be used as a host material of a phosphorescent material, and has higher light-emitting efficiency than the comparative example in which the compound CBP having $\Delta E_{ST}$ greater than 0.3 eV was used as the host material.

The compounds of the present disclosure have a D-A type molecular structure, which is advantageous for achieving effective separation of HOMO and LUMO. In particular, an adjacent connection between D unit and A unit through benzene and six-membered heteroaryl ring can increase a dihedral angle between D unit and A unit, such that a steric hindrance between D unit and A unit is relatively larger to obtain a smaller ΔEst. In addition, the structure of the compound according to the present disclosure can increase an intramolecular space-constraint effect, reduce a positive solvation discoloration effect of molecules, while improving the molecular luminescence color purity and achieving a smaller peak width at half height.

Figure 5:
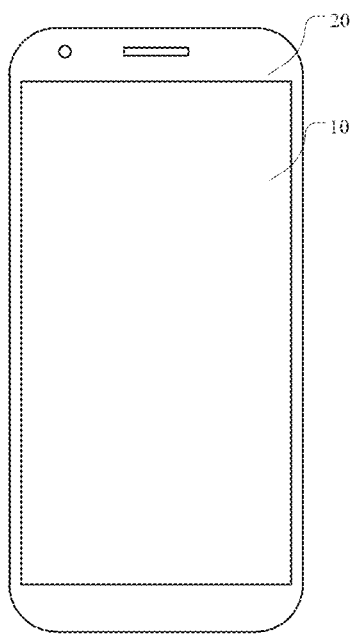
FIG. 5 is a structural schematic diagram of a display apparatus according to an embodiment of the present disclosure.

The present disclosure also provides a display apparatus including the organic light-emitting display panel described above. In the present disclosure, the organic light-emitting device can be an OLED, which is used in an organic light-emitting display apparatus. The organic light-emitting apparatus can be display screens of mobile phone, computer, liquid crystal display television, smart watch, smart car, VR or AR helmet display screen, and other smart devices. FIG. 5 is a schematic diagram of a display apparatus according to an embodiment of the present disclosure, in which the reference sign 10 denotes a display panel of mobile phone, and the reference sign 20 represents the display apparatus.

The above embodiments of the present disclosure are several preferred embodiments, but not intended to limit the scope of the claims. Various changes and modifications can be made by those skilled in the art without departing from the scope of the present application. The protection scope of the present disclosure is defined by the claims.

What is claimed is:

1. A compound, having a structure represented by Formula (1):

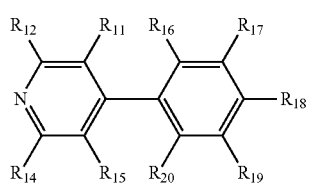

$R_{11}$-$R_{12}$ and $R_{14}$-$R_{20}$ are each selected from the group consisting of a hydrogen atom, a fluorine atom, alkyl, alkoxy, cyano, trifluoromethyl, an electron-accepting group, and an electron-donating group;

the electron-donating group is a substituted or unsubstituted C12-C40 carbazolyl; and the electron-accepting group is a cyano-containing group;

wherein among $R_{11}$-$R_{12}$ and $R_{14}$-$R_{15}$, at least one is the electron-donating group and at least one is the electron-accepting group; and among $R_{16}$-$R_{20}$, at least one is the electron-donating group and at least one is the electron-accepting group; and at least one of $R_{11}$ and $R_{15}$ is the electron-donating group or the electron-accepting group, and at least one of $R_{16}$ and $R_{20}$ is the electron-donating group or the electron-accepting group.

2. The compound according to claim 1, wherein the compound is selected from the following compounds:

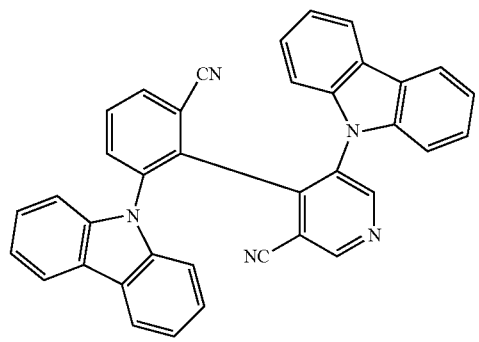

P18

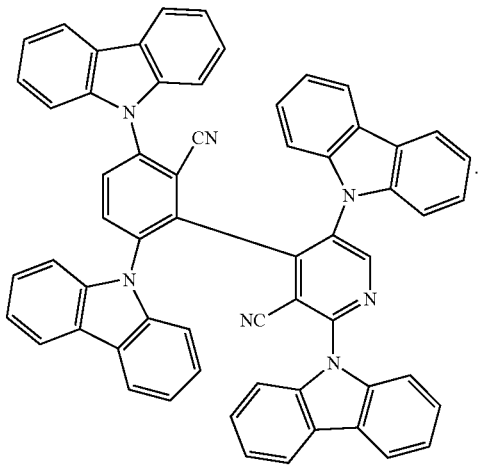

P28

3. A display panel, comprising an organic light-emitting device,
the organic light-emitting device comprising an anode; a cathode; and a light-emitting layer disposed between the anode and the cathode,
wherein a light-emitting material of the light-emitting layer comprises one or more of the compounds according to claim 1.

4. A display apparatus, comprising the display panel according to claim 3.

* * * * *